(12) United States Patent
Tom et al.

(10) Patent No.: US 6,657,065 B2
(45) Date of Patent: Dec. 2, 2003

(54) METHODS OF MAKING QUINOLINE AMIDES

(75) Inventors: Norma J. Tom, Waterford, CT (US); David C. Whritenour, Groton, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/131,711

(22) Filed: Apr. 23, 2002

(65) Prior Publication Data

US 2002/0161233 A1 Oct. 31, 2002

Related U.S. Application Data

(62) Division of application No. 09/924,665, filed on Aug. 8, 2001, now Pat. No. 6,417,367.
(60) Provisional application No. 60/224,366, filed on Aug. 11, 2000.

(51) Int. Cl.[7] ............................................. C07D 213/54
(52) U.S. Cl. ....................................................... 546/329
(58) Field of Search .......................................... 546/329

(56) References Cited

PUBLICATIONS

McDaniel, CA 107:183678, 1987.*
Oi, CA 122:305525, 1995.*
Touet, CA 123:256140, 1995.*
B. Singh, et al., *A Convenient Synthesis of 3–(4–Pyridinyl)quinolines,* J. Heterocyclic Chem., 28, pp. 1453–1454 (Aug.–Sep. 1991).
C. Cheng, et al., *The Friedlander Synthesis of Quinolines,* Organic Reactions, Chapter 2, pp. 37–201.
J.P. Wolfe, et al., *A Highly Active Catalyst for the Room–Temperature Amination and Suzuki Coupling of Aryl Chlorides,* Angew. Chem. Int. Ed., 38, No. 16, pp. 2413–2416 (1999).
M. Keshavarz–K, et al., *An Improved Isolation of Triformylmethane (TFM): Properties and Preparation of Some Derivatives.* Communications pp. 641–644 (Aug. 1988).
C. Jutz, et al., *Pyridine durch elektrocyclishen Ringsclub mit Eliminierung,* Communcations, pp. 326–328 (May 1977).
Z. Arnold, et al., *Synthetische Reaktiones Von Dimesthylformamid I. Allgemeine Synthese Von β–Dialdehyden,* Collection Czechoslov. Chem. Commun, 23 pp. 452–461 (1958).
M. Suzuki, et al., *Practical Synthesis of Quinoline Nucleus of NK–10,.* Heterocycles, 50, No. 1. pp. 478–483.
J.M.F. Gagan, et al., *Preparation of Quinoline from α–Methylene–ketones,* J. Chem. Soc., pp. 2488–2492 (1970).
C.G. Frost, et al., *Recent Developments in Aromatic Heteroatom Coupling Reactions,* J. Chem. Soc., pp. 2615–2623 (1998).
M. Selby, *A Review of Recent Advances in the Metal Medicated Synthesis of Aryl Ethers and the Arylation of Amines and Heterocycles,* Discovery Chemistry.

J.F. Hartwig, et al., *Room–Temperature Palladium–Catalyzed Amination of Aryl Bromides and Chlorides and Extended Scope of Aromatic C–N Bond Formation with a Commercial Ligan,.* J. Org. Chem., 64 pp. 5575–5580 (1999).
B.C. Hamann, et al., *Sterically Hindered Chelating Alkyl Phosphines Provide Large Rate Accelerations in Palladium–Catalyzed Amination of Aryl Iodides, Bromides, and Chlorides, and the First Amination of Aryl Tosylates,* J. Am. Chem. Soc., 120, pp. 7369–7370 (1998).
J. Huang, et al., *General and Efficient Catalytic Amination of Aryl Chlorides Using a Palladium/Bulky Nucleophilic Carbene System Organic Letters,.* 1, No. 8. pp. 1307–1309 (1999).
E. Brenner, et al., *New Efficient Nickel(0) Catalysed Amination of Aryl Chlorides, Tetrahedron Letters,.* 39, pp. 5359–5362 (1998).
C.A. Merlic, et al., *Structure Determination and Synthesis of Fluoro Nissl Green: An RNA–Binding Fluorochrome,* J. Org. Chem., 6 pp. 3365–3369 (1995).
C.C. Price, et al., *Synthesis of 4–Hydroxyquinolines. IX. 4–Chloro–7–cyanoquinoline and 4–Chloro–5– cyanoquinoline,* 69 pp. 374–376 (1947).
Z. Arnold, *Synthetic Reactions of Dimethylformamide. XII. Formylation of Some Carboxylic Acids and Their Derivatives, Collection Czechoslov. Chem. Commun.,* 26, pp. 3051–3059 (1961).
J. Kucera, et al., *Synthetic Reactions of Dimethylformamide. XXIV. Preparation of β–Dialdehyde Derivatives by a Formylation of Alkylmalonic Acids,* 32, pp. 3792–3793 (1967).
Z. Arnold, *Synthetic Reactions of Dimethylformamide. XXV. Preparation of Dimethylaminomalonaldehyde, 2–Methoxy–, 2–Ethoxy–and 2–Dimethylaminotrimethinium Salts, Collection Czechoslov. Chem. Commun.,* 38, pp. 1168–1172 (1973).

(List continued on next page.)

Primary Examiner—D. Margaret Seaman
(74) Attorney, Agent, or Firm—Peter C. Richardson; Gregg C. Benson; James T. Jones

(57) ABSTRACT

The present invention relates to methods of making quinoline amides of Formula I below, which are microsomal triglyceride transfer protein inhibitors and can be used as medicines.

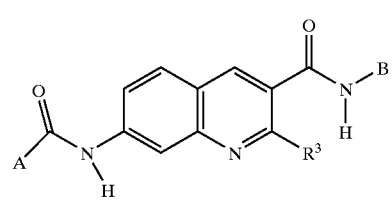

I

The present invention also relates to compounds that are used to make quinoline amides of Formula I and methods of making these compounds.

4 Claims, No Drawings

PUBLICATIONS

D. Lloyd, et al., *Vinamidines and Vinamidinium Salts—Examples of Stabilized Push–Pull Alkenes*, Angew. Chem. Int. Ed. Engl., 15, No. 8. pp. 459–468 (1976).

R. Ruggeri, et al., *7-[(4-Trifluoromethyl-Biphenyl-2-Carbonyl)Amino]Quinoline-3-Carboxylic Acid Amides, and Methods of Inhibitin the Secretion of Apolipoprotein B*. U.S. patent application No. 09/722,281, filed Nov. 9, 2000. Attorney Docket No. PC10601ATMC.

* cited by examiner

METHODS OF MAKING QUINOLINE AMIDES

CROSS-REFERENCE TO RELATED APPLICATIONS

This application is a divisional of U.S. application Ser. No. 09/924,665, filed Aug. 8, 2001, now U.S. Pat. No. 6,417,367. This application also claims priority of U.S. provisional application No. 60/224,366, filed Aug. 11, 2000.

FIELD OF THE INVENTION

The present invention relates to methods of making quinoline amides. The present invention also relates to compounds that are used to make quinoline amides and methods of making these compounds.

BACKGROUND OF THE INVENTION

Quinoline amides of Formula I and Ia ($R^3$ is hydrogen) below are microsomal triglyceride transfer protein (MTP) inhibitors and can be used to treat hypercholesterolemia, atherosclerosis, obesity, hyperlipidemia, hypertriglyceridemia, hypoalphalipoproteinemia, pancreatitis, diabetes, stroke, restenosis, or Syndrome X.

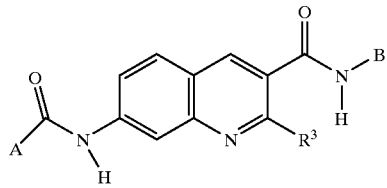

I wherein each $R^3$ is independently hydrogen or $C_1$–$C_6$alkyl;

A is

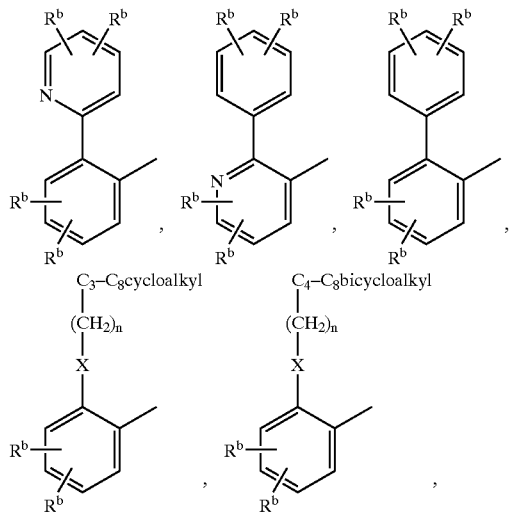

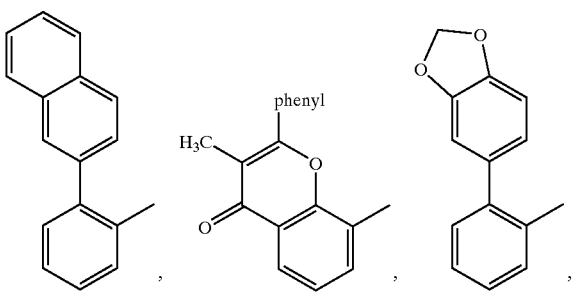

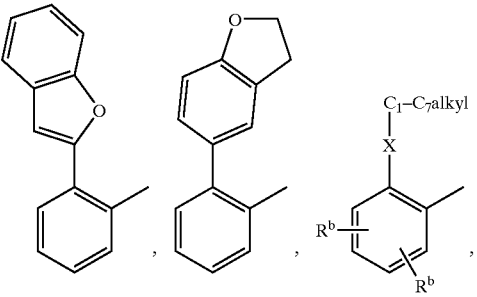

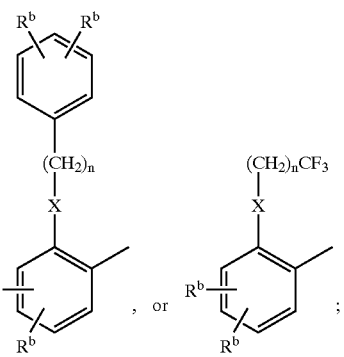

X is O or S;

n is 0 to 6;

each $R^b$ is independently hydrogen, —$CF_3$, —$OC_1$–$C_6$alkyl, halo, —SH, —$SC_1$–$C_6$alkyl, phenyl, or —$C_1$–$C_6$alkyl;

B is hydrogen,

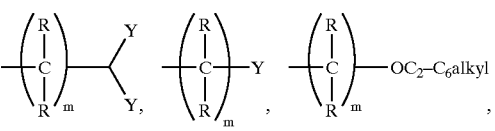

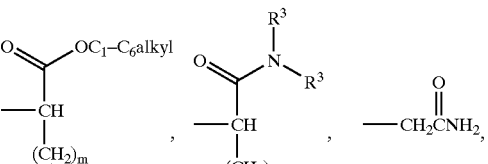

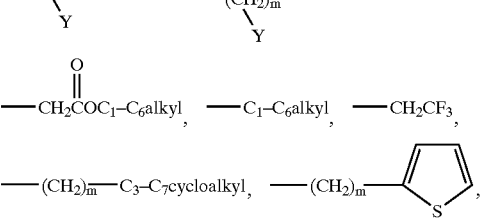

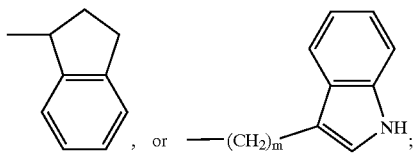

each R is independently hydrogen or $C_1$–$C_6$alkyl;
each Y is independently phenyl, substituted phenyl, pyridyl or substituted pyridyl, wherein from 1 to 3 substituents are independently selected from —$CF_3$, halo, —$OC_1$–$C_6$alkyl, or —$C_1$–$C_6$alkyl; and
m is 0 to 5.

U.S. patents that disclose MTP inhibitors include U.S. Pat. Nos. 5,919,795, 5,595,872, 5,721,279, 5,739,135, and 5,789,197.

U.S. provisional patent application No. 60/164,803 discloses compounds of Formula I and sets forth specific methods of making the compounds disclosed in the application by starting with 4-hydroxy-7-nitro-quinoline-3-carboxylic acid ethyl ester, which is a known compound [C. C. Price et al., *Journal of the American Chemical Society*, 69, 374–376 (1947)]. In one aspect, the present invention concerns improved methods of making compounds of Formula I. Unlike the method disclosed in the provisional application, the present methods do not require starting with 4-hydroxy-7-nitro-quinoline-3-carboxylic acid ethyl ester, which is made using a high temperature cyclization to form the quinoline ring system. In addition, the present methods require fewer steps and form the quinoline ring system directly.

SUMMARY OF THE INVENTION

The present invention provides a method of making a compound of Formula

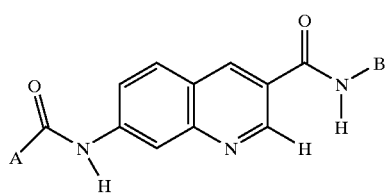

Ia wherein
each $R^3$ is independently hydrogen or $C_1$–$C_6$alkyl;
A is

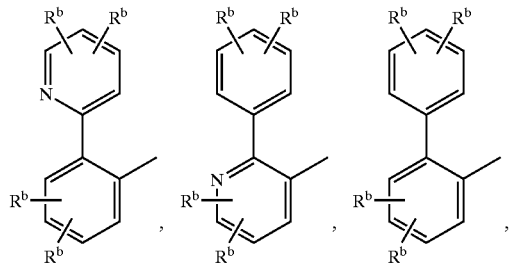

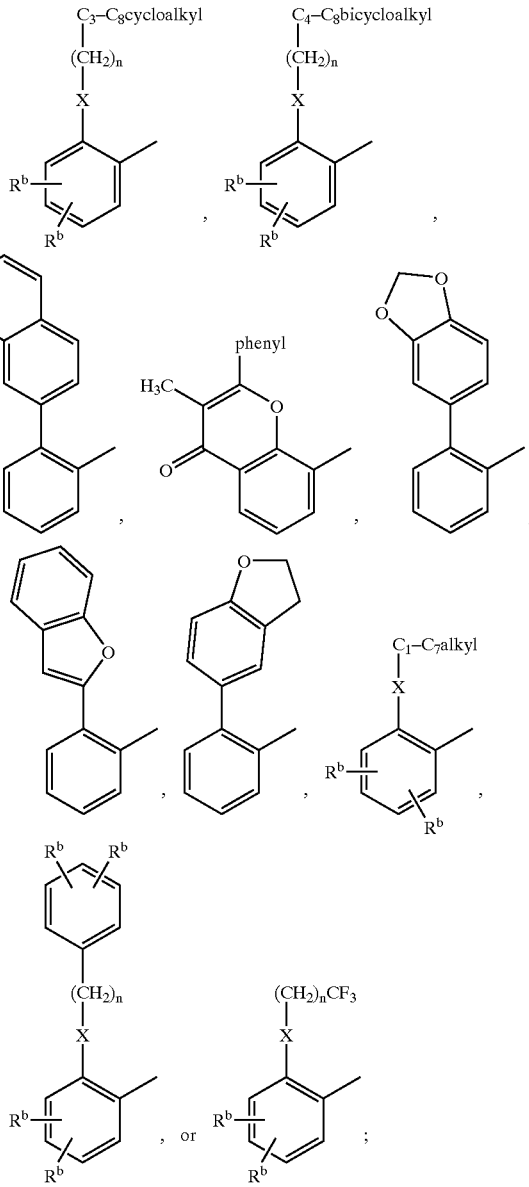

X is O or S;
n is 0 to 6;
each $R^b$ is independently hydrogen, —$CF_3$, —$OC_1$–$C_6$alkyl, halo, —SH, —$SC_1$–$C_6$alkyl, phenyl, or —$C_1$–$C_6$alkyl;
B is hydrogen,

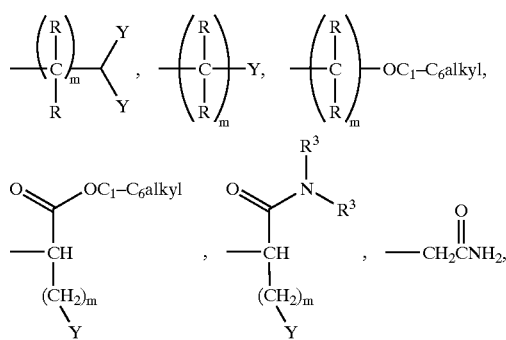

-continued

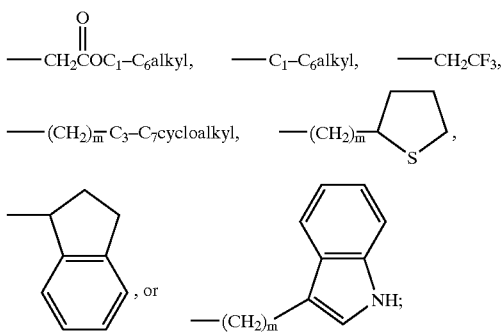

each R is independently hydrogen or $C_1$–$C_6$alkyl;

each Y is independently phenyl, substituted phenyl, pyridyl or substituted pyridyl, wherein any substituents are independently selected from —$CF_3$, halo, —$OC_1$–$C_6$alkyl, or —$C_1$–$C_6$alkyl; and m is 0 to 5;

the method comprising the steps of:

a. reacting

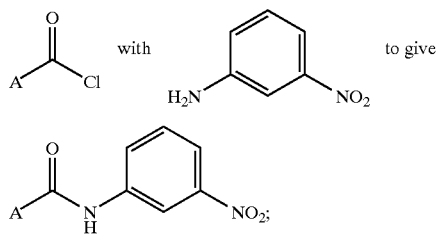

b. reducing

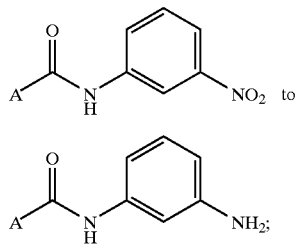

c. reacting

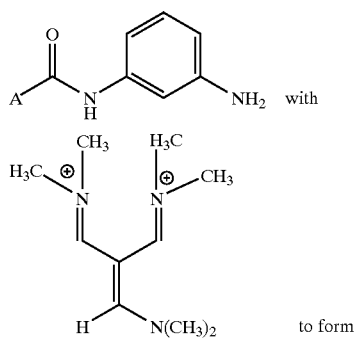

-continued

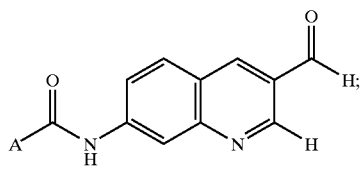

d. oxidizing

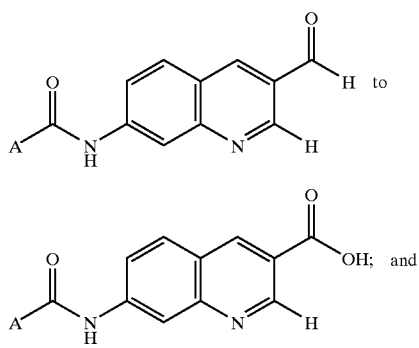

e. coupling

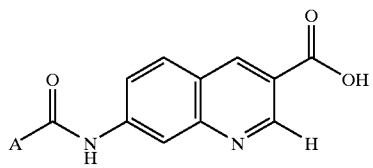

with $H_2N$—B to form a compound of Formula Ia.

In a preferred embodiment of the method, A is

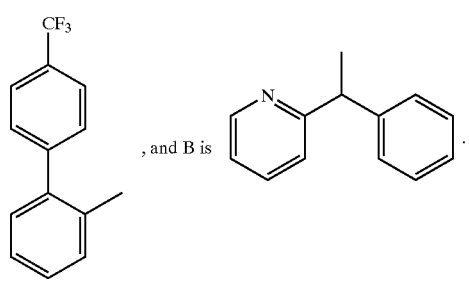

, and B is

The present invention also provides the compounds:

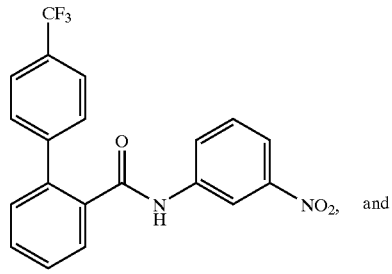

-continued
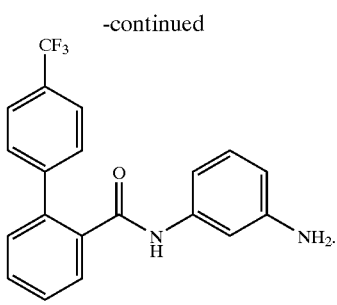
The present invention also provides the compound:
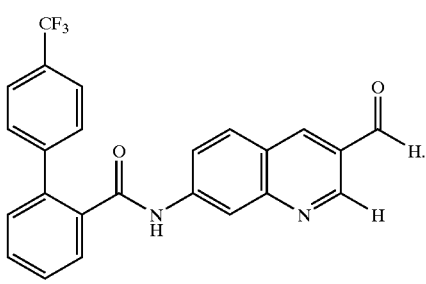
Also provided is a method of making
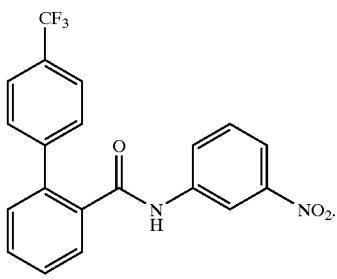
the method comprising the step of:
a. reacting
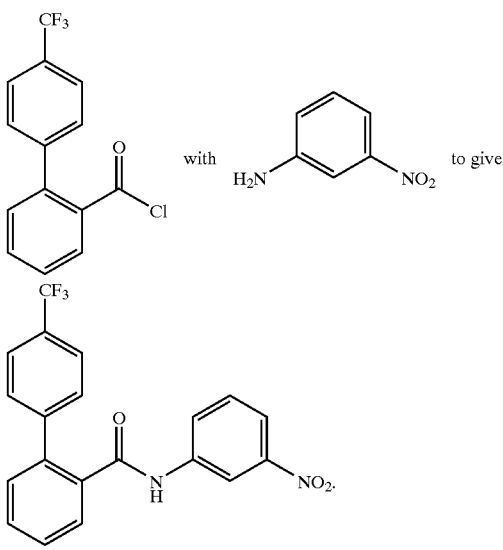
Also provided is a method of making
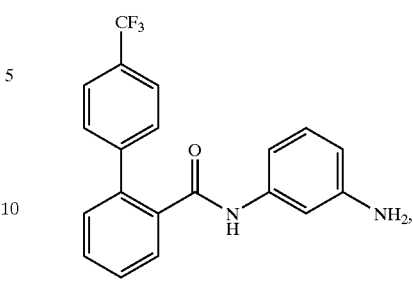
the method comprising the steps of:
a. reacting
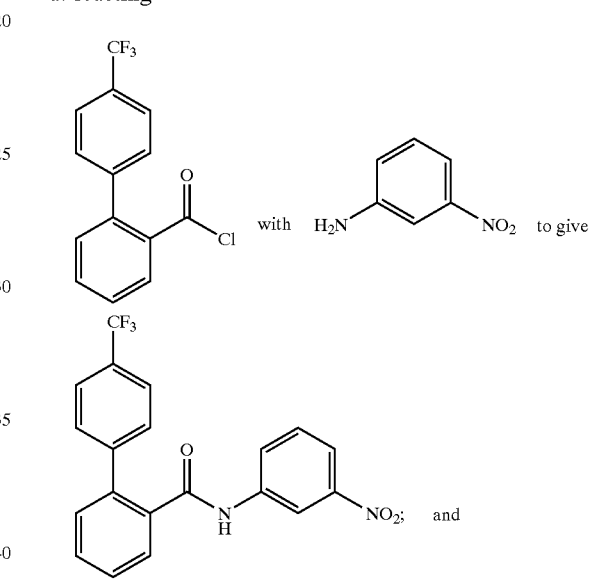
b. reducing
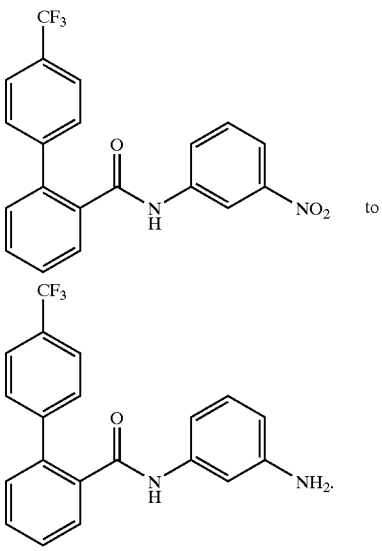

Also provided is a method of making
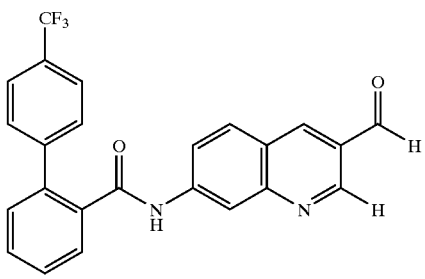
the method comprising the steps of:
a. reacting
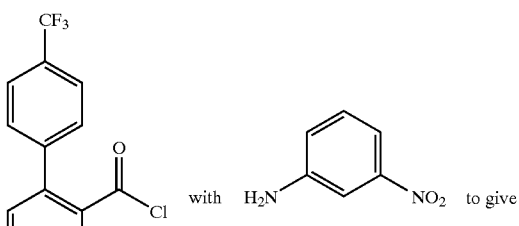
b. reducing
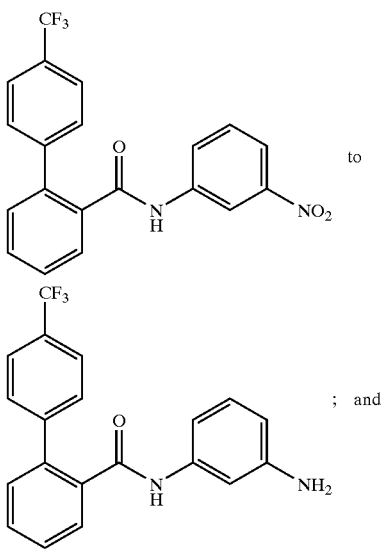
c. reacting
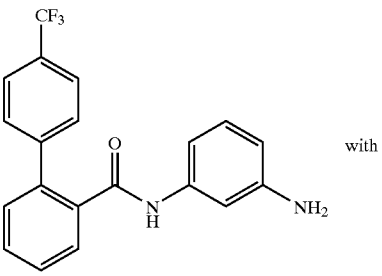
to form
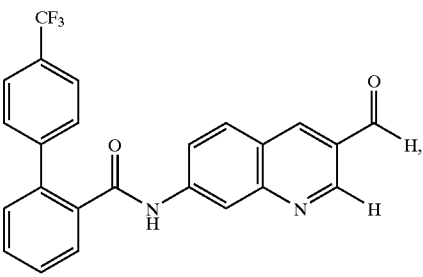
Also provided is a method of making
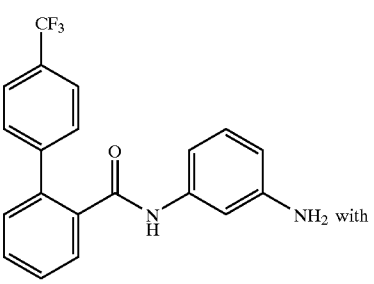
the method comprising the step of:
reacting -continued
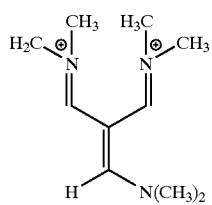
to form
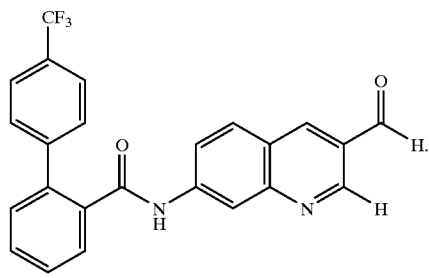
Also provided is a method of making a compound of Formula I
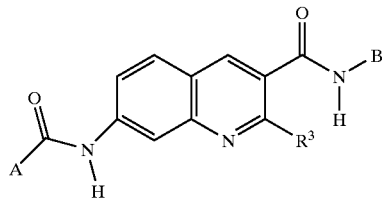
I
wherein
each $R^3$ is independently hydrogen or $C_1$–$C_6$alkyl;
A is
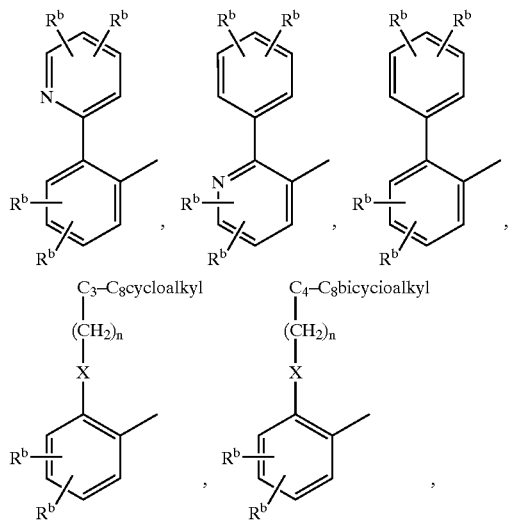
-continued
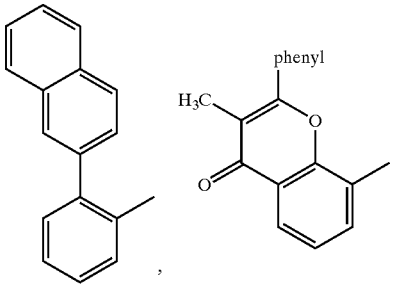
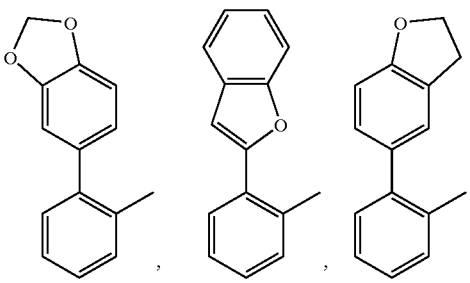
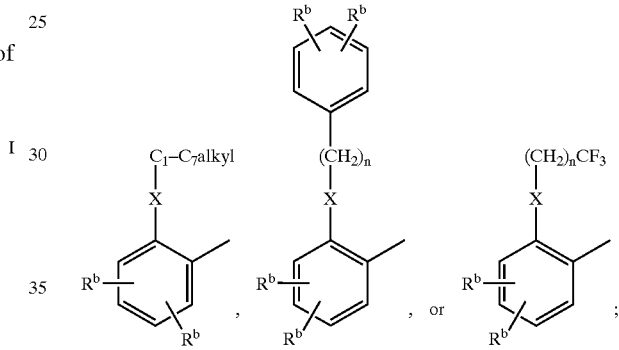
X is or S;
n is 0 to 6;
each $R^b$ is independently hydrogen, —$CF_3$, —$OC_1$–$C_6$alkyl, halo, —SH, —$SC_1$–$C_6$alkyl, phenyl, or —$C_1$–$C_6$alkyl;
B is hydrogen,
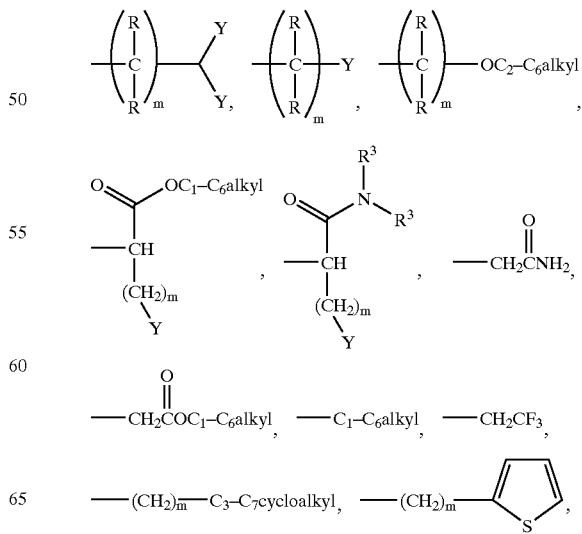

-continued

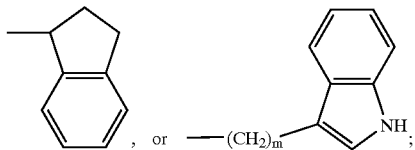, or —(CH₂)ₘ—;

each R is independently hydrogen or $C_1-C_6$alkyl;
each Y is independently phenyl, substituted phenyl, pyridyl or substituted pyridyl, wherein any substituents are independently selected from —$CF_3$, halo, —$OC_1-C_6$alkyl, or —$C_1-C_6$alkyl; and
m is 0 to 5;
the method comprising the steps of:

1. reacting

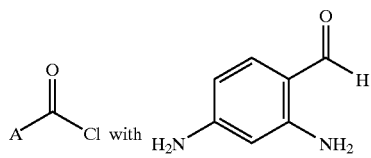

to form

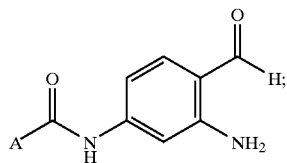

2. reacting

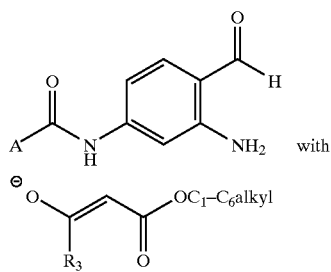

to give

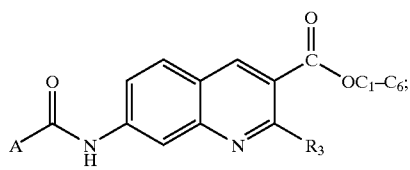

3. hydrolyzing

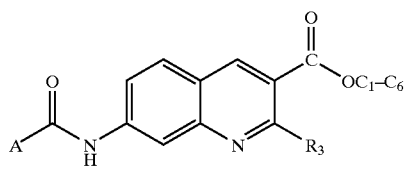

to give

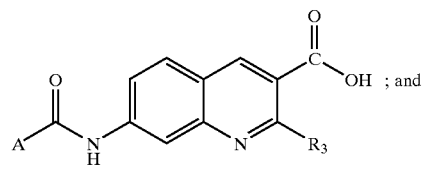

4. reacting

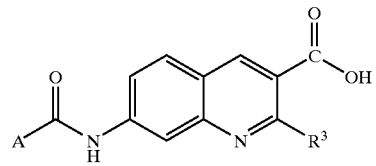

with $H_2N$—B to provide a compound of Formula I.

In a preferred embodiment of the method, in step 1, the compound poly(4-vinylpyridine) is used a base.

In another preferred embodiment of the method, in step 2 the

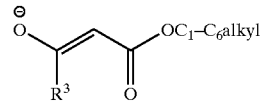

is the sodium salt and $C_1-C_6$alkyl is ethyl.

In another preferred embodiment of the method, $R^3$ is hydrogen, A is

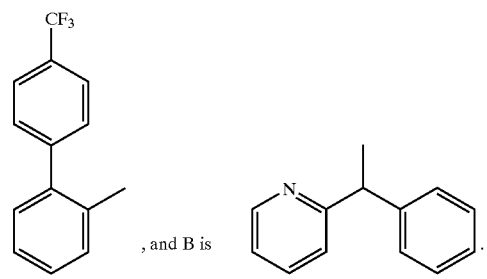, and B is

Also provided is the compound:

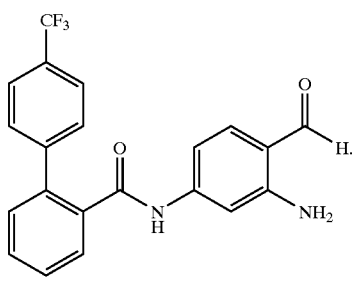

Also provided is a method of making
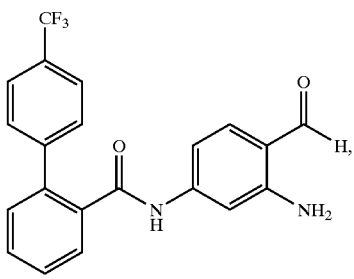
the method comprising the step of:
reacting
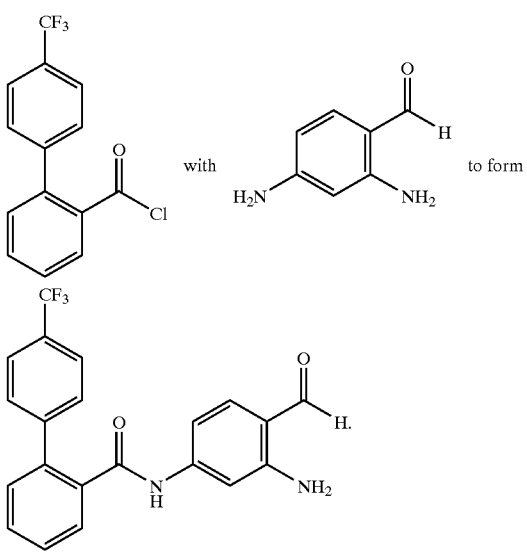
Also provided is a method of making a compound of Formula I
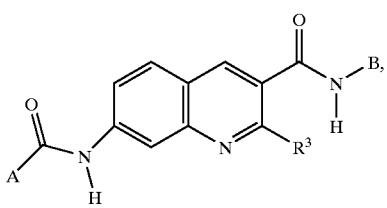
wherein
each $R^3$ is independently hydrogen or $C_1$–$C_6$alkyl;
A is
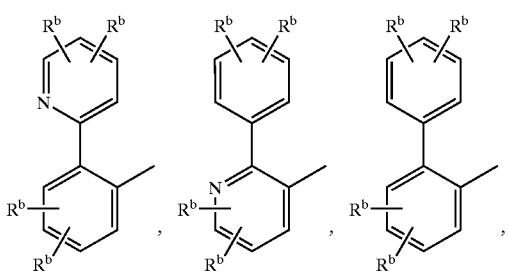
-continued
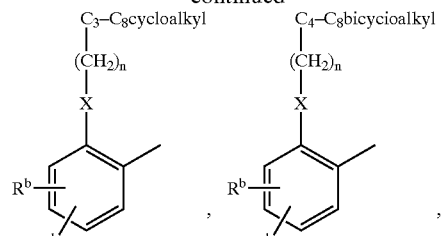
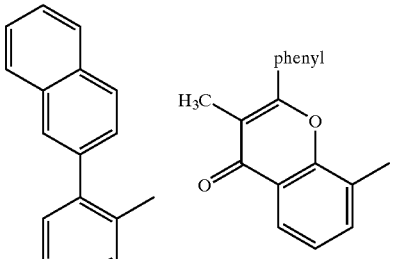
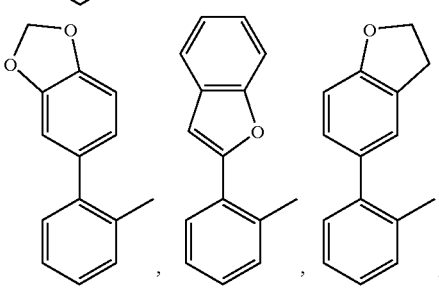
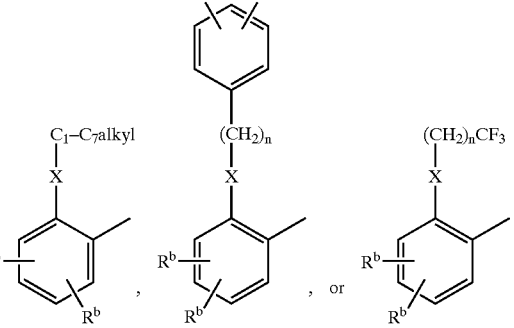
X is O or S;
n is 0 to 6;
each $R^b$ is independently hydrogen, —$CF_3$, —$OC_1$–$C_6$alkyl, halo, —SH, —$SC_1$–$C_6$alkyl, phenyl, or —$C_1$–$C_6$alkyl;
B is hydrogen,
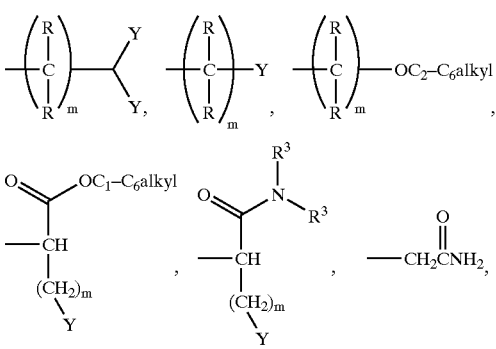

-continued

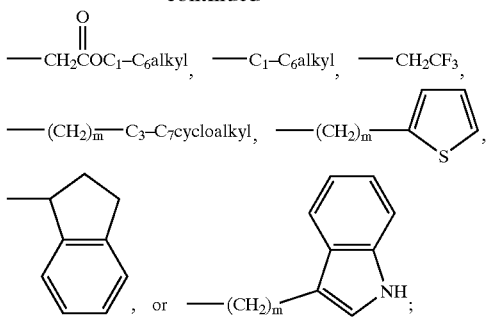

each R is independently hydrogen or $C_1$–$C_6$alkyl;
each Y is independently phenyl, substituted phenyl, pyridyl or substituted pyridyl, wherein any substituents are independently selected from —$CF_3$, halo, —$OC_1$–$C_6$alkyl, or —$C_1$–$C_6$alkyl; and
m is 0 to 5;
the method comprising the steps of:

A. reacting

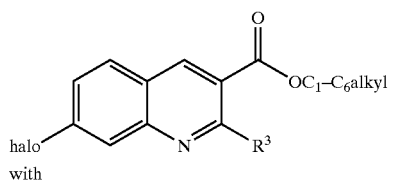

with

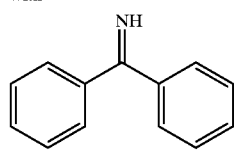

to form

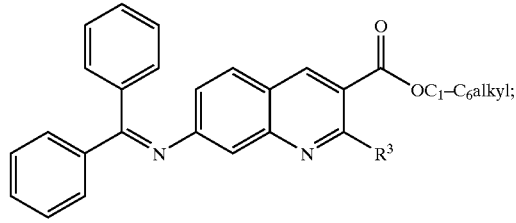

B. hydrolyzing

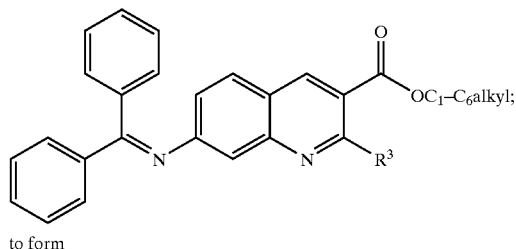

to form

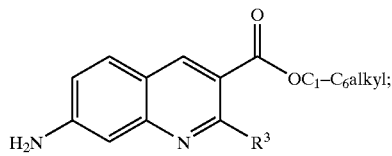

C. reacting

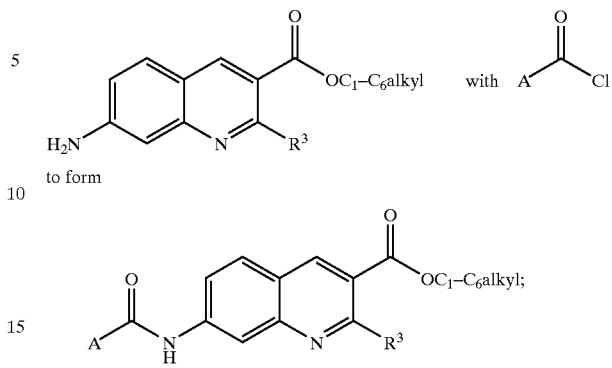

to form

D. hydrolyzing

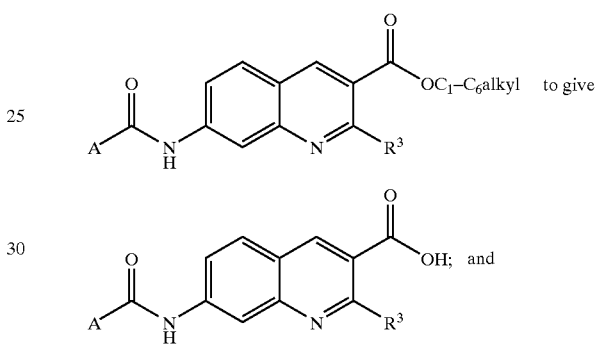

to give

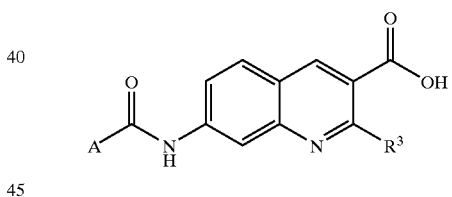

OH; and

E. reacting

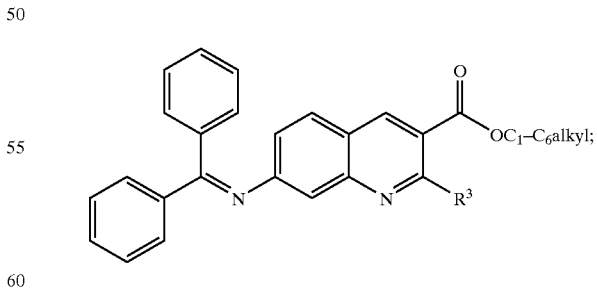

with $H_2N$—B to provide a compound of Formula I.
The present invention also provides the compounds:

wherein $R^3$ is hydrogen or $C_1$–$C_6$alkyl.

In a preferred embodiment of the immediately preceding compounds, $R^3$ is hydrogen and $C_1$–$C_6$ alkyl is ethyl.

Also provided is a method of making

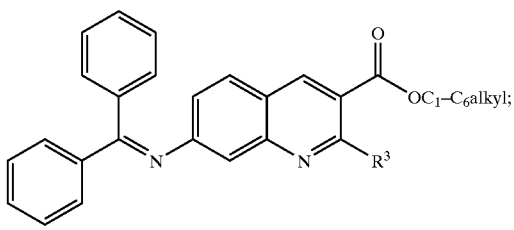

wherein R³ is hydrogen or $C_1$–$C_6$alkyl,
the method comprising the steps of:
a. reacting

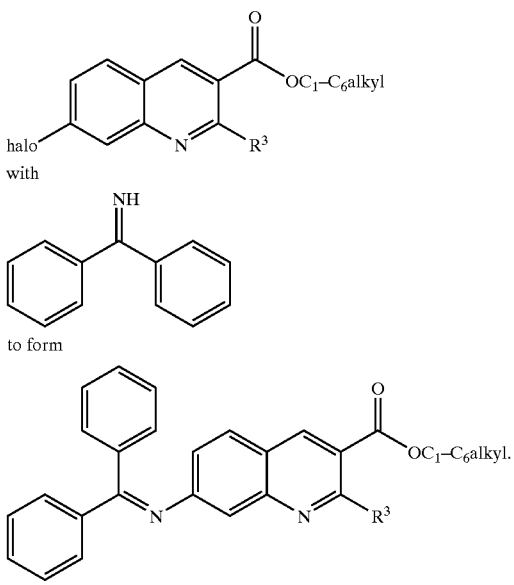

Also provided is a method of resolving phenyl-(2-pyridyl)-methylamine to obtain (S)-phenyl-(2-pyridyl)-methylamine, (S)-(+)-α-methoxyphenylacetic acid salt, the method comprising the steps of:
a. reacting phenyl-(2-pyridyl)-methylamine
with (S)-(+)-α-methoxyphenylacetic acid in isopropanol, which results in a precipitate being formed; and
b. isolating the precipitate, which is (S)-phenyl-(2-pyridyl)-methylamine, (S)-(+)-α-methoxyphenylacetic acid salt.

In a preferred embodiment of the resolution method, the (S)-(+)-α-methoxyphenylacetic acid is present in the reaction in an amount in the range of about 0.5 equivalents with respect to the amine.

In another preferred embodiment of the resolution, the isolated precipitate is purified by recrystallization.

DETAILED DESCRIPTION OF THE INVENTION

The present invention provides methods of making compounds of Formula I and Formula Ia (R³ is hydrogen). The compounds of Formula I and Ia are inhibitors of microsomal triglyceride transfer protein (MTP) and can be used as pharmaceutical agents to treat diseases such as hypercholesterolemia, atherosclerosis, obesity, hyperlipidemia, hypertriglyceridemia, hypoalphalipoproteinemia, pancreatitis, diabetes, stroke, restenosis, and Syndrome X.

In addition, the present invention provides compounds that are intermediates used in the synthesis of compounds of Formula I and Ia and methods of making these intermediates.

The following terms are used in the application and are defined below.

The term "alkyl" means a straight or branched chain hydrocarbon. Representative examples of alkyl groups include methyl, ethyl, propyl, isopropyl, butyl, isobutyl, tert-butyl, sec-butyl, pentyl, and hexyl. Preferred alkyl groups are $C_1$–$C_6$alkyl.

The term "halogen" or "halo" means fluorine, chlorine, bromine or iodine.

The term "cycloalkyl" means a cyclic hydrocarbon. Examples of cycloalkyl groups include cyclopropyl, cyclobutyl, cyclopentyl, cyclohexyl and cycloheptyl.

The term bicycloalkyl means a cyclic hydrocarbon that contains bridging atoms. Examples of bicycloalkyl groups include bicyclo [3.2.1] octane and bicyclo [1.1.0] butane.

The symbol "—" means a covalent bond.

In one embodiment, the present invention provides a method of making compounds of Formula Ia,

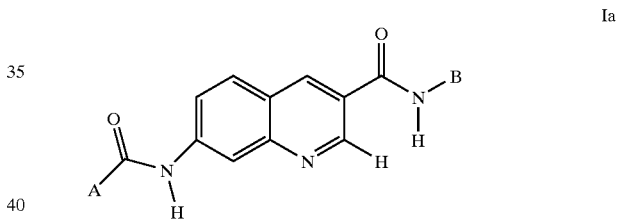

Ia wherein each R³ is independently hydrogen or $C_1$–$C_6$alkyl;
A is

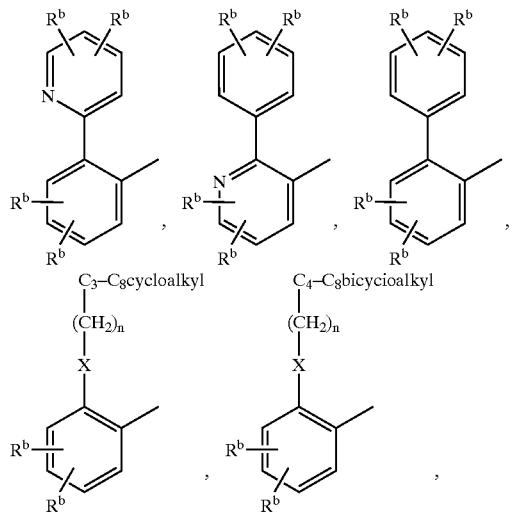

-continued

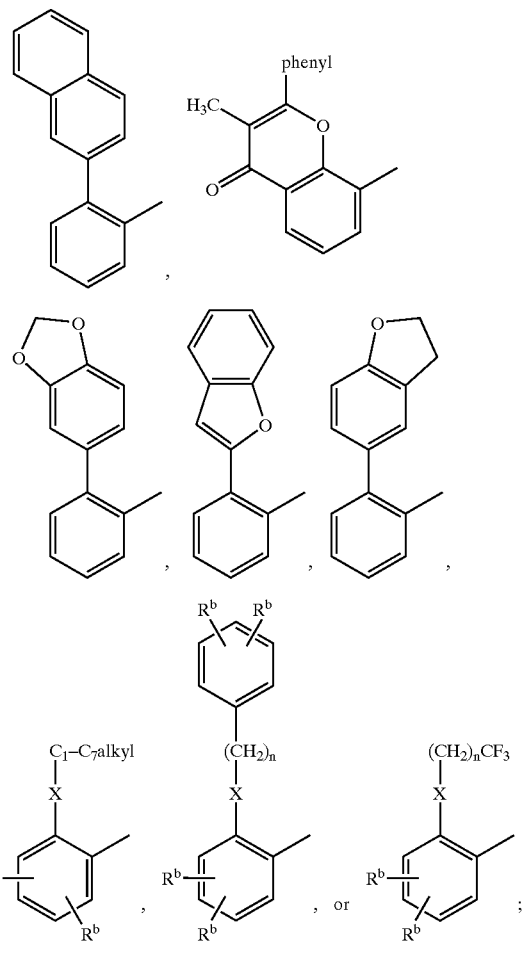

X is O or S;
n is 0 to 6;
each $R^b$ is independently hydrogen, —$CF_3$, —$OC_1$–$C_6$alkyl, halo, —SH, —$SC_1$–$C_6$alkyl, phenyl, or —$C_1$–$C_6$alkyl;
B is hydrogen,

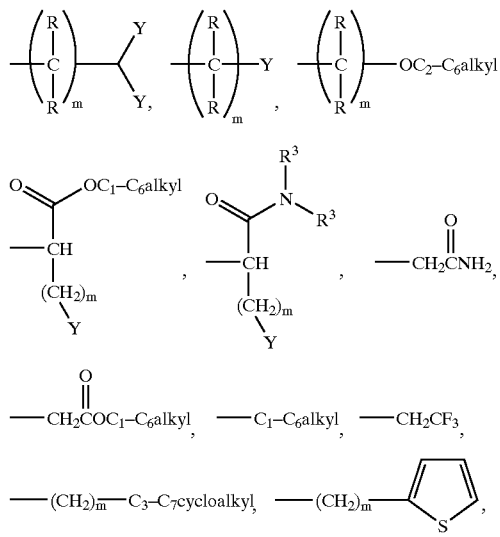

-continued

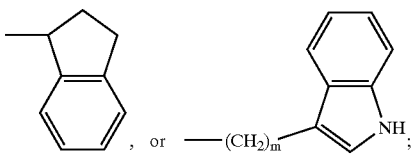

each R is independently hydrogen or $C_1$–$C_6$alkyl;
each Y is independently phenyl, substituted phenyl, pyridyl or substituted pyridyl, wherein any substituents are independently selected from —$CF_3$, halo, —$OC_1$–$C_6$alkyl, or —$C_1$–$C_6$alkyl; and
m is 0 to 5;
the method comprising the steps of:
a. reacting

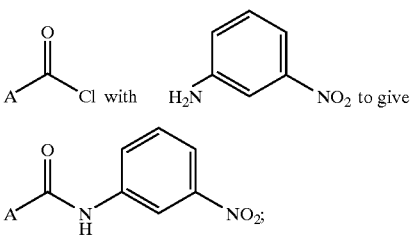

b. reducing

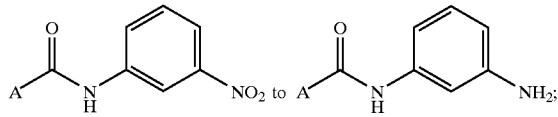

c. reacting

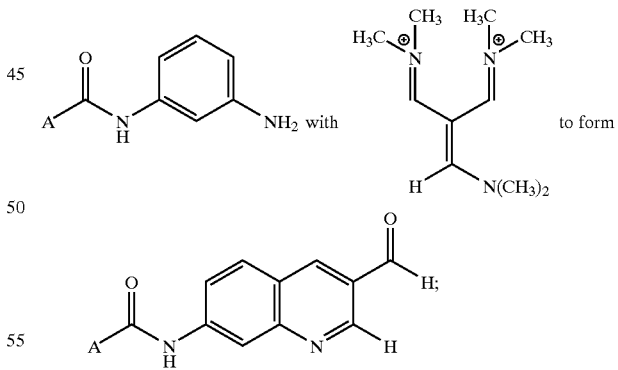

d. oxidizing

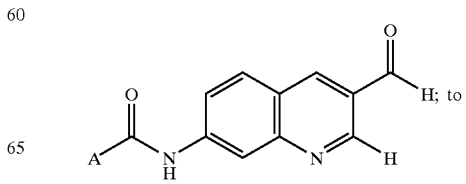

-continued

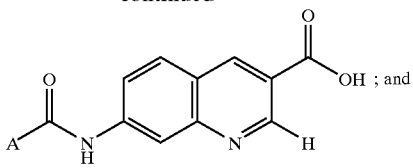

e. coupling

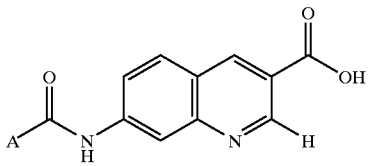

with H$_2$N—B to form a compound of Formula Ia.

In step a of the above method, the nitro amide compound can be made by coupling 3-nitroaniline (Aldrich, Milwaukee, Wis.) with an acid chloride. An acid chloride, which is an activated carboxylic acid, can be made from the corresponding carboxylic acid following procedures that are well known in the art. A preferred acid chloride is 4'-trifluoromethyl-biphenyl-2-carbonyl chloride. Examples of reagents that can be used to make an acid chloride (or acid halide) from an acid include oxalyl chloride, thionyl chloride, PCl$_3$, PBr$_3$, Ph$_3$P in CCl$_4$, and cyanuric fluoride. The coupling of an amine with a carboxylic acid (typically, an activated carboxylic acid such as an acid chloride) is well known in the art. A preferred coupling method of step a of the present invention uses a base such as triethylamine in a polar, aprotic solvent such as tetrahydrofuran. Many procedures that couple a carboxylic acid or derivative with an amine to form an amide have been reported. Many involve the activation of a carboxylic acid to an acid chloride or anhydride followed by coupling with an amine. Many coupling reagents directly activate an acid for reaction with an amine including carbodiimides such as dicyclohexylcarbodiimide (DCC), propanephosphonic anhydride, and various hydroxybenzotriazole derivatives. In many cases it is possible to interconvert from other carboxylic acid derivatives such as an ester, nitrile, or amide to the desired amide. These methods are summarized in Richard C. Larock, *Comprehensive Organic Transformations*, 2nd ed, Wiley, N.Y., 1999, pp. 1941–1949,1953–1957, 1978–1982,1988–1990, and 1973–1976.

In step b of the above method, the nitro amide made in step a is reduced to an amino amide. The reduction of a nitro group to an amino group is well known to those skilled in the art. For example, in a preferred embodiment of the present invention, palladium dihydroxide (also known as Pearlman's catalyst) and ammonium formate in a mixture of isopropanol and ethyl acetate can be used. The reduction of an aryl nitro group to an aryl amine has been accomplished in many ways. Common methods include the reduction with a metal catalyst such as palladium on carbon or Rainey nickel and hydrogen gas. Transfer hydrogenation with hydrazine/graphite or cyclohexene/palladium is also effective. Other hydride sources, such as sodium borohydride with various metal salts and lithium aluminum hydride may also be used. Nitro reductions have also been accomplished with zinc or tin and hydrochloric acid. These methods and others are summarized by Richard C. Larock in *Comprehensive Organic Transformations*, 2nd ed, Wiley, N.Y., 1999, pp. 821–828.

In step c of the above method, a quinoline ring system is formed by reacting the amino amide produced in step b with the diamine reagent (2-dimethylaminomethylene-1,3-bis(dimethylimmonio)propane):

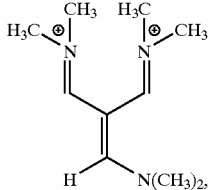

preferably the bis(tetrafluoroborate) salt (2BF$_4^-$). The diamine reagent used in this step can be prepared by reacting bromoacetic acid or bromoacetyl chloride with phosphorus oxychloride and N,N-dimethylformamide, followed by tetrafluoroboric acid. The generation of this reagent is set forth specifically below. The use of this reagent to form the quinoline ring system is advantageous because it does not require a high temperature cyclization step.

In step d above, the newly formed quinoline, which contains an aldehyde group, is oxidized to form a quinoline carboxylic acid. The oxidation of an aldehyde group to a carboxylic acid group is well known to those skilled in the art. A preferred oxidation method of the present invention uses sodium chlorite. Other reagents than can be used to oxidize an aldehyde to a carboxylic acid include potassium permanganate, sodium periodate, ruthenium tetroxide, chromium trioxide, hydrogen peroxide, sodium perchlorate, or the like.

Next, the quinoline carboxylic acid formed in step d above is coupled with an amine having the formula H$_2$N—B. The coupling of an amine with a carboxylic acid to form an amide is well known to those skilled in the art. A preferred coupling method of the present invention uses 1-(3-dimethylaminopropyl)-3-ethylcarbodiimide hydrochloride, 1-hydroxybenzotriazole, triethylamine, and dichloromethane. A preferred amine is phenyl-(2-pyridyl)-methylamine. Many procedures to convert a carboxylic acid or derivative to an amide have been reported as described above.

The present invention is also directed to a method of making compounds of Formula I:

I

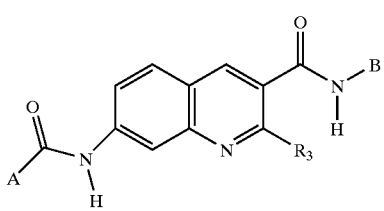

wherein each R³ is independently hydrogen or $C_1$–$C_6$alkyl;
A is

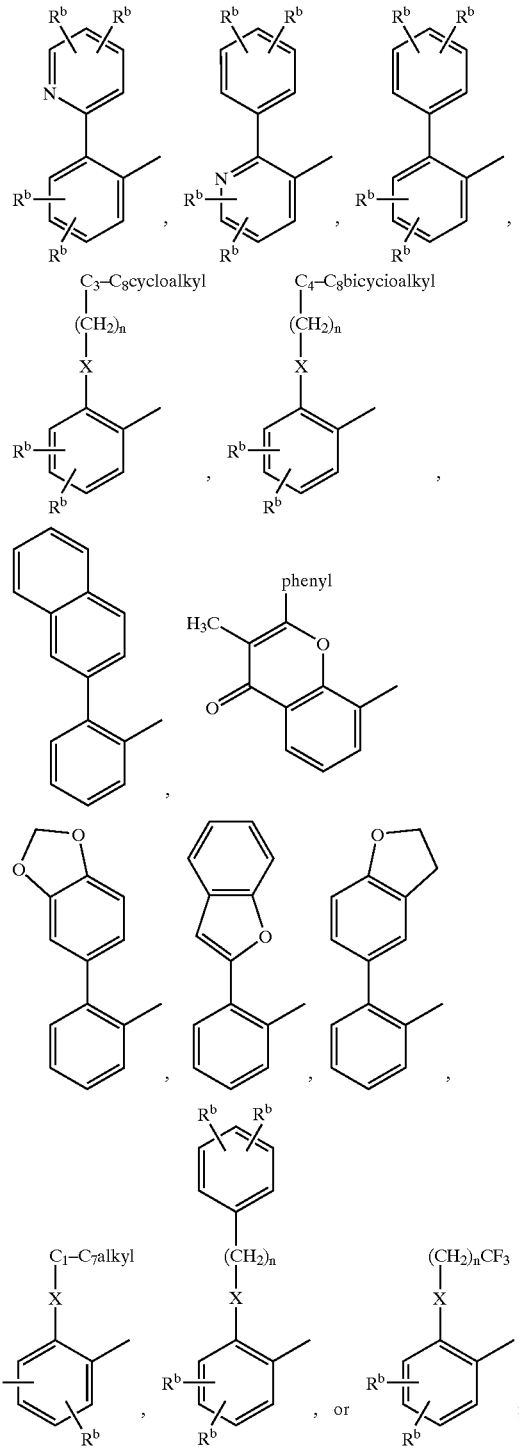

X is O or S;
n is 0 to 6;
each $R^b$ is independently hydrogen, —$CF_3$, —$OC_1$–$C_6$alkyl, halo, —SH, —$SC_1$–$C_6$alkyl, phenyl, or —$C_1$–$C_6$alkyl;

B is hydrogen,

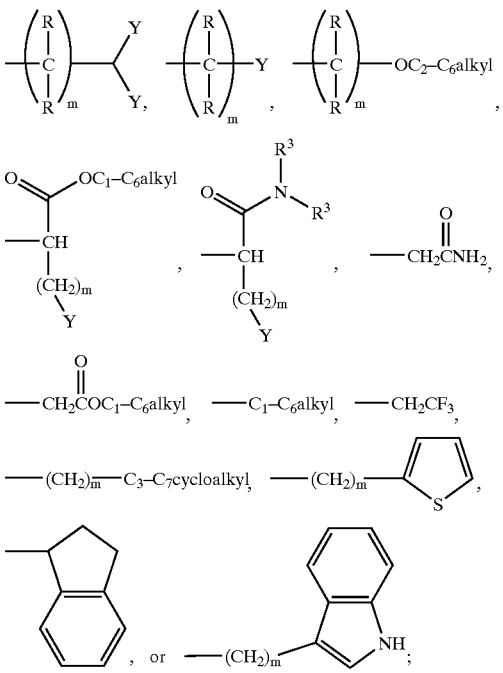

each R is independently hydrogen or $C_1$–$C_6$alkyl;
each Y is independently phenyl, substituted phenyl, pyridyl or substituted pyridyl, wherein any substituents are independently selected from —$CF_3$, halo, —$OC_1$–$C_6$alkyl, or —$C_1$–$C_6$alkyl; and
m is 0 to 5;

the method comprising:

1.) reacting

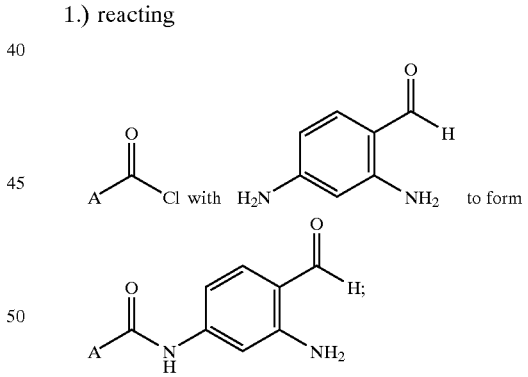

to form

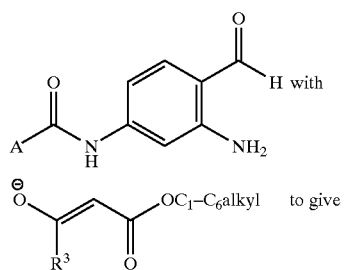

2. reacting

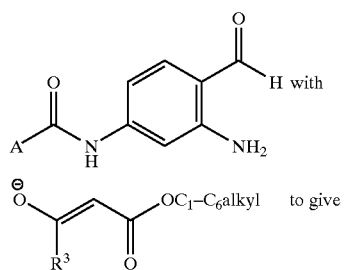 with $^{\ominus}O$—...—$OC_1$–$C_6$alkyl   to give

-continued

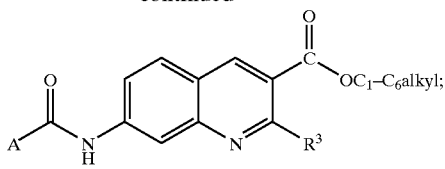

3. hydrolyzing

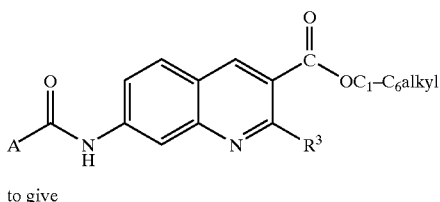

to give

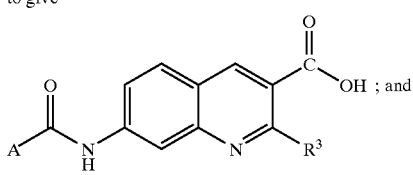

4. reacting

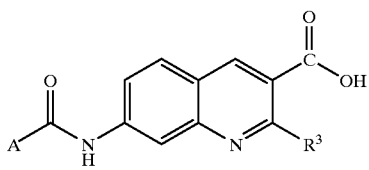

with H$_2$N—B to provide a compound of Formula I.

In step 1 above, an amino aldehyde amide is formed by reacting an acid chloride with 2,4-diaminobenzaldehyde, which is a known compound. [See, for example, Merlic, C. A. et al., *J. Org. Chem.*, 1995, 60, 3365–3369.]. The acid chloride can be formed from the corresponding carboxylic acid by procedures that are well known in the art. 2,4-Diaminobenzaldehyde can also be obtained by reducing 2,4-dinitrobenzaldehyde (Aldrich, Milwaukee, Wis.). Reductions of a nitro group to an amino group are well known. A preferred reduction uses iron dust, glacial acetic acid and ethyl acetate. The reduction of an aryl nitro group to an aryl amine has been accomplished in many ways. Common methods include the reduction with a metal catalyst such as palladium on carbon or Rainey nickel and hydrogen gas. Transfer hydrogenation with hydrazine/graphite or cyclohexene/palladium is also effective. Other hydride sources such as sodium borohydride with various metal salts and lithium aluminum hydride may be used. Nitro reductions have also been accomplished with zinc or tin and hydrochloric acid. These reactions and others are summarized by Richard C. Larock in *Comprehensive Organic Transformations*, 2nd ed, 1999, pp. 821–828.

The formation of the amino aldehyde amide is accomplished by coupling an acid chloride with an amino group of 2,4-diaminobenzaldehyde. In a preferred embodiment of the method, the coupling is accomplished using poly(4-vinylpyridine). The poly(4-vinylpyridine) (CAS#9017-40-7) can be obtained as 2% or 25% crosslinked with divinylbenzene from Aldrich, Milwaukee, Wis. The use of poly(4-vinylpyridine) provides for greater selectivity with regard to reaction at the 4-amino group of the 2,4-diaminobenzaldehyde.

In step 2 above the amino aldehyde amide is reacted with

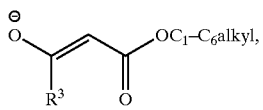

preferably the sodium salt, to provide a quinoline ester. The reaction can be run in glacial acetic acid.

In step 3 above, the quinoline ester is hydrolyzed to form a quinoline carboxylic acid. The hydrolysis of esters is well known to those skilled in the art. Preferred reagents that can be used include a base such as sodium hydroxide in a mixture of methanol and tetrahydrofuran. Other reagents that can be used to hydrolyze an ester to a carboxylic acid include lithium hydroxide, potassium hydroxide or barium hydroxide in methanol, tetrahydrofuran or mixtures thereof. Additional reagents that can be used are set forth in *Organic Reactions*, 1976, 24, 187; and E. Haslam in *Tetrahedron*, 1980, 36, 2409–2433.

In step 4 above, the quinoline carboxylic acid is coupled with an amine H$_2$N—B to provide a compound of Formula I. A preferred amine is phenyl-(2-pyridyl)-methylamine. Many procedures to couple a carboxylic acid or derivative with an amine to form an amide have been reported as described above.

The compounds of Formula I can also be synthesized by the following procedure:

A. reacting

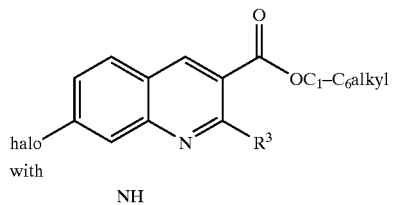

with

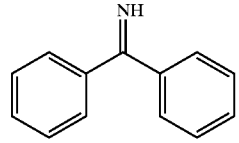

to form

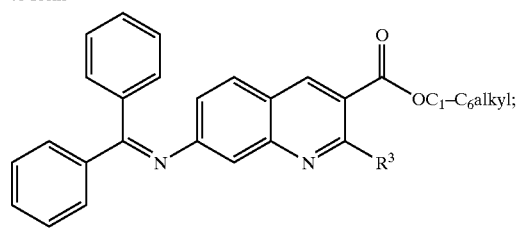

B. hydrolyzing

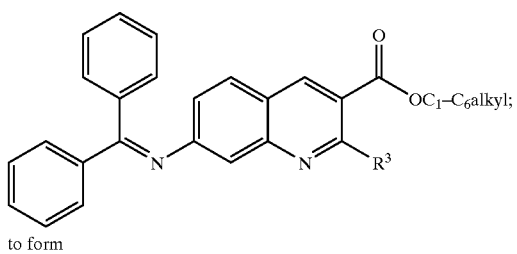

to form

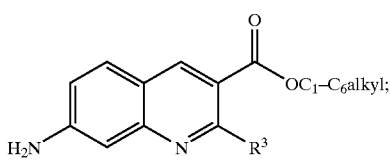

to form

C. reacting

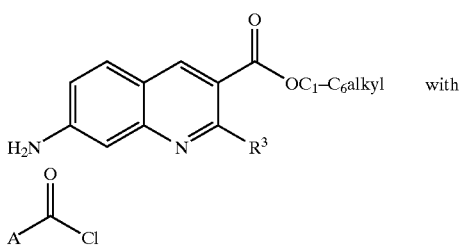

to form

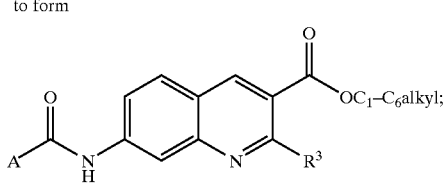

D. hydrolyzing

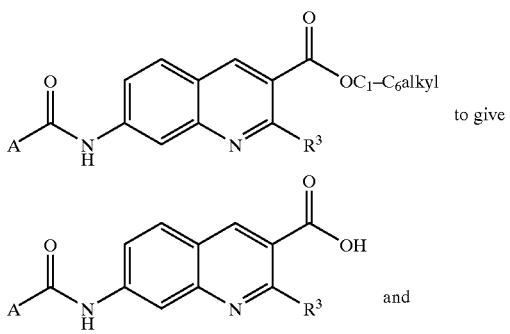

E. reacting

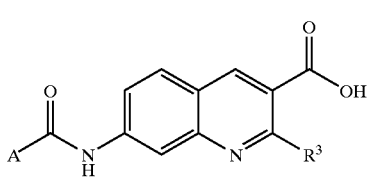

with H$_2$N—B to provide a compound of Formula I.

In step A above, a halo quinoline ester is reacted with benzophenone imine to form a benzhydrylidene amino quinoline ester. Preferred reagents used to accomplish the reaction include benzophenone imine, tri (dibenzylidieneacetone)dipalladium, 2-(dicyclohexylphosphino)biphenyl, and sodium tert-butoxide in toluene. The halo quinoline ester is known. See, for example, Silva, Y. et al., *Acta Cient Venez.*, 41, 130–131 (1990). Alternatively, the halo quinoline ester can be made by reducing 4-chloro-2-nitrobenzaldehyde to 4-chloro-2-aminobenzaldehyde. 4-Chloro-2-nitrobenzaldehyde can be obtained from P.H.T. International, Inc., Charlotte, N.C. The reduction of a nitro group to an amino group is well known to those skilled in the art. Examples of additional suitable reagents are set forth above. A preferred reduction uses iron powder, hydrochloric acid and a solvent of aqueous ethanol. Next, the 4-chloro-2-aminobenzaldehyde is reacted with 3-hydroxy-acrylic acid ethyl ester, sodium salt, to form the halo quinoline ester.

In step B above, the benzhydrylidene amino quinoline ester is hydrolyzed to form an amino quinoline ester. Preferred hydrolysis reagents are hydrochloric acid and ethanol. Other hydrolysis reagents include mineral acids and water, hydrogen and palladium on carbon, and hydroxylamine.

In step C above, the amino quinoline ester is reacted with an acid chloride to form an amide quinoline ester. Preferred reaction conditions include diisopropylamine in CH$_2$Cl$_2$. The reaction of an acid chloride (i.e., an activated carboxylic acid) with an amine to form an amide is well known to those skilled in the art, and other suitable reagents are set forth above.

In step D above, the amide quinoline ester is hydrolyzed to form an amide quinoline carboxylic acid. Preferred reagents include sodium hydroxide in methanol and tetrahydrofuran. Other reagents that can be used to hydrolyze an ester to a carboxylic acid include lithium hydroxide, potassium hydroxide, barium hydroxide in methanol or tetrahydrofuran or mixtures thereof. Other examples of ester hydrolysis are set forth in *Organic Reactions*, 1967, 24, 187; and *Tetrahedron*, 1980, 36, 2409.

In step E above, the amide quinoline carboxylic acid is reacted with an amine of formula HN—B to form a compound of Formula I.

In another aspect, the present invention provides a method of resolving phenyl-(2-pyridyl)-methylamine to obtain the (S)-phenyl-(2-pyridyl)-methylamine, (S)-(+)-α-methoxyphenylacetic acid salt. The resolution method comprises the steps of combining racemic phenyl-(2-pyridyl)-methylamine, which can be obtained from Alfa Aesar, Ward Hill, Mass., and (S)-(+)-α-methoxyphenylacetic acid from Aldrich, Milwaukee, Wis., in isopropanol, which results in the formation of a precipitate, which is (S)-phenyl-(2-pyridyl)-methylamine, (S)-(+)-α-methoxyphenylacetic acid salt. The precipitate is isolated, and can be recrystallized using isopropanol one or more times. Each recrystallization results in a greater enantiomeric purity of the desired (S) isomer of the phenyl-(2-pyridyl)-methylamine salt. It is preferable if about 0.5 mole equivalents of the (S)-(+)-α-methoxyphenylacetic acid is used with regard to the phenyl-(2-pyridyl)-methylamine.

The (S)-phenyl-(2-pyridyl)-methylamine, (S)-(+)-α-methoxyphenylacetic acid salt can be converted to (S)-phenyl-(2-pyridyl)-methylamine hydrochloride salt as detailed below.

All documents cited herein are hereby incorporated by reference.

The examples presented below are intended to illustrate particular embodiments of the invention and are not intended to limit the scope of the specification, including the claims, in any manner.

The following abbreviations are used herein

| AcOH | Acetic Acid |
|------|-------------|
| EtOH | Ethanol |
| EtOAc | Ethyl Acetate |
| DMF | Dimethylformamide |
| THF | Tetrahydrofuran |
| MeOH | Methanol |
| mol | Mole(s) |
| equiv | Equivalent(s) |
| TLC | Thin layer chromatography |
| HPLC | High pressure liquid chromatography |
| IPO | Isopropanol |
| IPE | diisopropylether |
| Et | Ethyl |
| APCl | Atmospheric pressure chemical ionization |
| Ph | Phenyl |

EXAMPLES

The following procedures illustrate the methods of making compounds of Formula I or Ia.

Method 1

Step 1

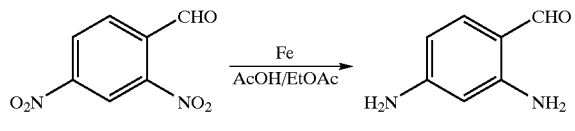

2,4-Diaminobenzaldehyde

To a nitrogen purged 5 liter 4-neck flask fitted with a condenser, mechanical stirrer, addition funnel, and temperature probe, was added 325 mesh iron dust, which can be obtained from Aldrich, Milwaukee, Wis. (220 g, 3.9 mol, 8 equiv), water (800 mL), and glacial acetic acid (5 mL). Over the next hour, some frothing occurred and the temperature rose to 28° C. In a separate container, 2,4-dinitrobenzaldehyde (97 g, 0.49 mol, 1 equiv) was dissolved in 1:1 glacial acetic acid/ethyl acetate (800 mL). 2,4-Dinitrobenzaldehyde can be purchased from Aldrich, Milwaukee, Wis. About 5 mL of the 2,4-dinitrobenzaldehyde solution was added dropwise to the iron mixture, which led to a dissipation of the frothing. The reaction mixture was warmed to 35° C. with a steam bath. Without further heating, the remaining dinitrobenzaldehyde solution was added at such a rate as to maintain the temperature below 50° C. The addition was completed after 6 hours. The reaction mixture was diluted with water (1 L) and diatomaceous earth (BNL Fine Chemicals and Reagents, Meriden, Conn.) was added (100 g). The reaction mixture was stirred an additional 3 hours at which point the temperature had dropped to 25° C. The solids were removed by filtration. The organic layer was separated and the aqueous layer was extracted with ethyl acetate (3×400 mL). The extracts were then used to wash the solids from the initial filtration. The organic layers were combined and washed with water (400 mL) and saturated aqueous $NaHCO_3$ (3×400 mL). The combined organic layers were dried over $MgSO_4$ and Darco G-60® (activated charcoal; BNL Fine Chemicals and Reagents, Meriden, Conn.) (10 g). After filtration to remove the drying agents, the organic layers were concentrated in vacuo to a slurry and diluted with 1 L of hexanes. The precipitated solids were collected by suction filtration and dried in air to give 2,4-diaminobenzaldehyde (48 g, 71%) as a light yellow solid.

$^1$H NMR (acetone-$d_6$) δ5.48 (br s, 2H), 5.94 (d, 1H, J=1.9 Hz), 6.08 (dd, 1H, J=2.0, 8.6 Hz), 6.75 (br s, 2H), 7.20 (d, 1H, J=8.6 Hz), 9.51 (s, 1H).

Step 2

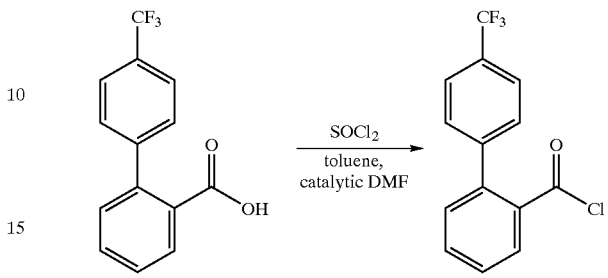

4'-Trifluoromethyl-biphenyl-2-carbonyl chloride

To a nitrogen purged 3 liter 4-neck flask fitted with a condenser, mechanical stirrer, temperature probe, and connected to a 2M aqueous NaOH scrubber was added toluene (1 L), 4'-trifluoromethyl-biphenyl-2-carboxylic acid (250 g, 0.94 mol, 1 equiv), and DMF (5 mL). 4'-Trifluoromethyl-biphenyl-2-carboxylic acid can be obtained from Aldrich, Milwaukee, Wis. The solution was heated to 60° C. and thionyl chloride (110 mL, 1.5 mol, 1.6 equiv) was added at such a rate as to maintain the temperature below 65° C. The addition was complete after 30 minutes and the reaction was heated to reflux. After 4 hours, the heating was stopped and the reaction was allowed to stir overnight at room temperature. The reaction mixture was concentrated in vacuo and the residue was used in the next step without further purification. The material crystallized to a solid at room temperature.

$^1$H NMR (CDCl$_3$) δ7.37 (dd, 1H, J=1.1, 7.6 Hz), 7.43 (d, 2H, J=8.1 Hz), 7.55 (td, 1H, J=1.3, 7.7 Hz), 7.66 (td, 1H, J=1.3, 7.5 Hz), 7.68 (d, 2H, J=8.1 Hz), 8.11 (dd, 1H, J=1.2, 7.9 Hz).

Step 3

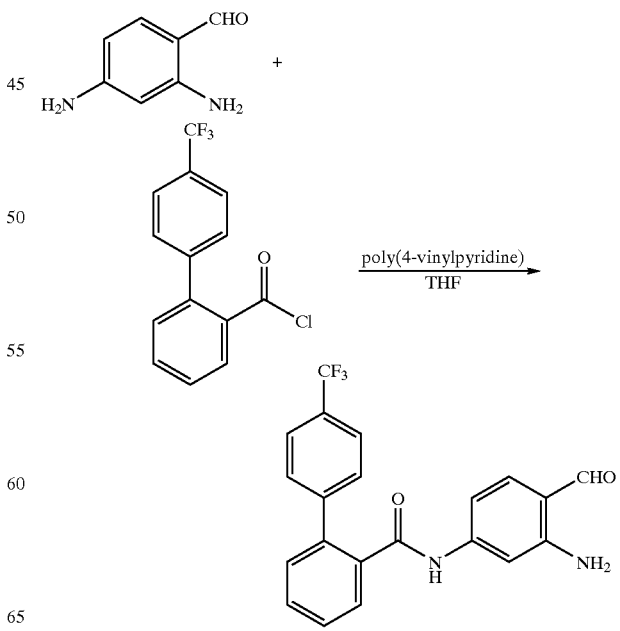

4'-Trifluoromethyl-biphenyl-2-carboxylic acid (3-amino-4-formyl-phenyl)-amide To a nitrogen purged 12 liter 3-neck flask fitted with a mechanical stirrer and temperature probe was added THF (4.3 L) and 2,4-diaminobenzaldehyde (50 g, 0.37 mol, 1 equiv). After cooling the solution to −70° C. (dry ice/acetone bath), poly(4-vinylpyridine), which can be obtained from Aldrich, Milwaukee, Wis., 25% cross-linked, (210 g) was added. A solution of 4'-trifluoromethyl-biphenyl-2-carbonyl chloride (105 g, 0.37 mol, 1 equiv) in THF (1 L) was added at such a rate as to maintain the temperature below −60° C. The light orange reaction mixture was allowed to warm to room temperature over 4 hours to give a dark red reaction mixture. (HPLC analysis showed an 18:1 mixture of mono- (retention time (rt)=4.8 min) to di- (rt=3.1 min) acylated products along with 5% residual starting material (rt=18.8 min), (Zorbax SIL (150 mm) from Agilent Technologies, Palo Alto, Calif. 2 mL/min 90:10 hexanes/isopropanol, 0.1% diethylamine, 250 nm, 40° C.). The reaction was quenched with 1 N NaOH (450 mL) and allowed to stir overnight at 25° C. The reaction mixture was filtered and the solids were washed with ethyl acetate (5×200 mL) and the combined organic layers were concentrated in vacuo to give a brown oil. The oil was dissolved in $CH_2Cl_2$ (1.5 L) and silica gel (EM Science, Gibbstown, N.J., 230–400 mesh or 0.04–0.06 mm particle size) (410 g) and Darco G-60® (10 g, BNL Fine Chemicals and Reagents) were added. The slurry was stirred for 15 minutes and filtered. The silica was washed with $CH_2Cl_2$ (5×200 mL). The combined organic layers were concentrated in vacuo and the methylene chloride was displaced with 1:1 hexanes/diisopropylether. The precipitated product was collected by suction filtration and dried in air to give 4'-trifluoromethyl-biphenyl-2-carboxylic acid (3-amino-4-formyl-phenyl)-amide (40 g, 30%, 43:1 mono-:bis acylated by HPLC) as a light yellow solid.

MS(APCI)385(M+1)$^+$; 383(M−1)$^{-1}$H NMR (DMSO-$d_6$) δ6.65 (dd, 1H, J=1.7, 8.7 Hz), 7.15 (br s, 2H), 7.25 (s, 1H), 7.38 (d, 1H, J=8.7 Hz), 7.46–7.68 (m, 6H), 7.74 (d, 2H, J=8.3 Hz), 9.57 (s, 1H), 10.51 (s, 1H).

Step 4

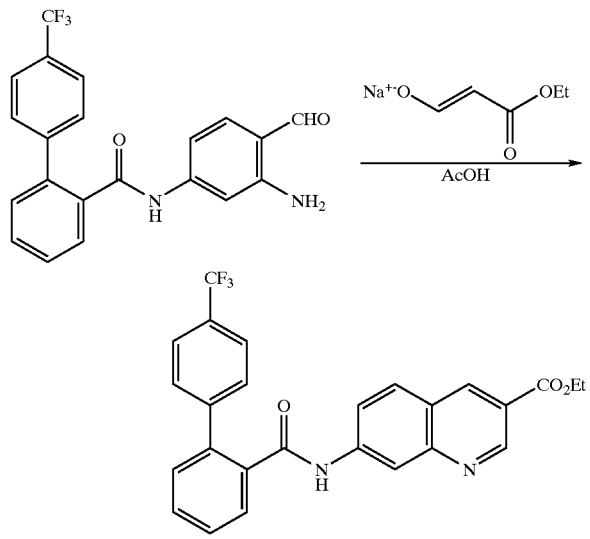

7-[(4'-Trifluoromethyl-biphenyl-2-carbonyl)-amino]-quinoline-3-carboxylic acid ethyl ester A solution of 4'-trifluoromethyl-biphenyl-2-carboxylic acid (3-amino-4-formyl-phenyl)-amide (7 g, 18.2 mmol, 1 equiv) and 3-hydroxy-acrylic acid ethyl ester, sodium salt (2.52 g, 18.2 mmol, 1 equiv) in glacial acetic acid (70 mL, 10 volumes) was heated at 80° C. for 2 hours. Additional 3-hydroxy-acrylic acid ethyl ester, sodium salt (2.52 g, 18.2 mmol, 1 equiv) was added and the solution heated for 15 hours. Again, additional 3-hydroxy-acrylic acid ethyl ester, sodium salt (1.26 g, 9.1 mmol, 0.5 equiv) was added and the solution heated for another 4 hours. The reaction mixture was concentrated in vacuo. The residue was dissolved in EtOAc (300 mL) and the organic layer was washed with a saturated aqueous sodium carbonate solution (2×200 mL) and 1 N NaOH solution (200 mL). The combined aqueous layers were back extracted with ethyl acetate (200 mL). The combined organic layers were dried over sodium sulfate and treated with Darco G-60® (7 g). The solids were removed by filtration and the filtrate was concentrated to afford crude 7-[(4'-trifluoromethyl-biphenyl-2-carbonyl)-amino]-quinoline-3-carboxylic acid ethyl ester, which was used in the next step without further purification.

MS(APCI)465(M+1)$^+$; 463 (M−1)$^{-1}$H NMR (DMSO-$d_6$) δ1.34 (t, 3H, J=7.1 Hz), 4.36 (q, 2H, J=7.1 Hz), 7.53–7.73 (m, 9H), 8.08 (d, 1H, J=8.7 Hz), 8.44 (d, 1H, J=1.3 Hz), 8.84 (d, 1H, J=2.1 Hz), 9.21 (d, 1H, J=2.1 Hz), 10.95 (s, 1H).

Step 5

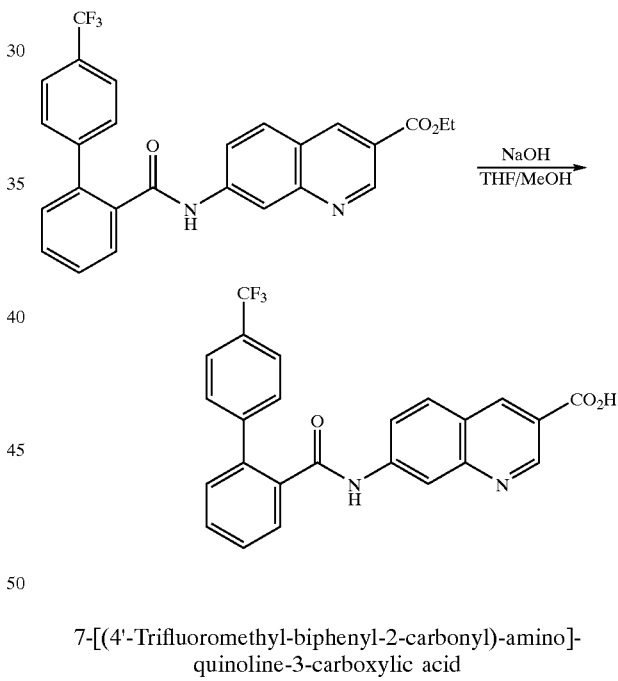

7-[(4'-Trifluoromethyl-biphenyl-2-carbonyl)-amino]-quinoline-3-carboxylic acid To a solution of 7-[(4'-trifluoromethyl-biphenyl-2-carbonyl)-amino]-quinoline-3-carboxylic acid ethyl ester (8.45 g, 18.2 mmol, 1 equiv) in MeOH (85 mL) and THF (85 mL) was added 1 N NaOH (91 mL, 91 mmol, 5 equiv). The solution was stirred at room temperature for 4 hours. The organic layer was removed in vacuo and the aqueous layer was washed with EtOAc (100 mL). The aqueous layer was then acidified to a pH of about 4 with concentrated HCl and a precipitate formed. The mixture was stirred for 48 hours and the solids collected by filtration to provide 7-[(4'-trifluoromethyl-biphenyl-2-carbonyl)-amino]-quinoline-3-carboxylic acid (4.5 g, 57% over two steps) as a yellow solid.

MS(APCI)437(M+1)+; 435(M−1)−1H NMR (DMSO-d6) δ7.54–7.74 (m, 9H), 8.08 (d, 1H, J=8.7 Hz), 8.44 (s, 1H), 8.84 (d, 1H, J=1.7 Hz), 9.22 (d, 1H, J=2.0 Hz), 10.90 (s, 1H).

Step 6

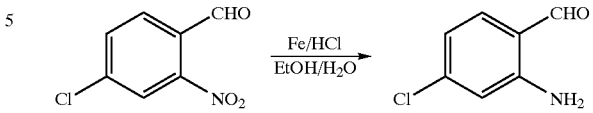

(+)-(S)-7-[(4'-Trifluoromethyl-biphenyl-2-carbonyl)-amino]-quinoline-3-carboxylic acid (phenyl-pyridin-2-yl-methyl)-amide To a suspension of 7-[(4'-trifluoromethyl-biphenyl-2-carbonyl)-amino]-3-carboxylic acid (10 g, 22.9 mmol, 1 equiv) and methylene chloride (168 mL, 16.8 volumes) was added (S)-phenyl-(2-pyridyl)-methylamine, hydrochloric acid salt (6.5 g, 29.8 mmol, 1.3 equiv), 3-ethyl-1-(3-diethylaminopropyl)-carbodiimide hydrochloride (EDAC) (5.3 g, 27.5 mmol, 1.2 equiv), and hydroxy benzotriazole (HOBT) (3.3 g, 24.1 mmol, 1.05 equiv). Diisopropylethylamine was added dropwise (11.97 g, 92.6 mmol, 4.04 equiv). The resulting solution was allowed to stir for 12 hours at room temperature. The solution was then extracted with 0.5 N hydrochloric acid (3×80 mL), saturated sodium hydrogen carbonate (2×80 mL) and saturated sodium chloride (80 mL). The organic layer was dried over sodium sulfate and concentrated in vacuo to give (+)-(S)-7-[(4'-trifluoromethyl-biphenyl-2-carbonyl)-amino]-quinoline-3-carboxylic acid (phenyl-pyridin-2-yl-methyl)-amide (12.2 g, 88.4%).

Method 2

Step 1

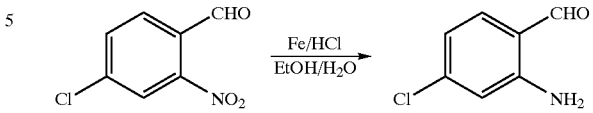

4-Chloro-2-aminobenzaldehyde

To a 3-neck flask fitted with a reflux condenser and a mechanical stirrer, were added 4-chloro-2-nitrobenzaldehyde (25 g, 135 mmol, 1 equiv), ethanol (375 mL), and water (100 mL). 4-Chloro-2-nitrobenzaldehyde can be obtained from P. H. T. International, Inc., Charlotte, N.C. Iron dust (225 mesh, Aldrich, Milwaukee, Wis.) (22.6 g, 405 mmol, 3 equiv) and concentrated hydrochloric acid (5.7 mL, 67.5 mmol, 0.5 equiv) was added. The slurry was heated to 85° C. for two hours, cooled to room temperature, filtered through diatomaceous earth and rinsed with ethanol (100 mL) and toluene (100 mL). The solution was transferred to a separatory funnel and toluene (300 mL) were added. The organic layer was washed with saturated sodium bicarbonate solution (300 mL) and brine (300 mL), then dried over sodium sulfate and then concentrated to provide 4-chloro-2-aminobenzaldehyde (17.4 g, 83%) as a yellow solid.

1H NMR (CDCl3) δ7.58 (dd, 1H, J=2.1, 8.7 Hz), 7.89 (d, 1H, J=8.7 Hz), 8.17 (s, 1H), 8.83 (d, 1H, J=1.7 Hz), 9.45 (br s, 2H).

Step 2

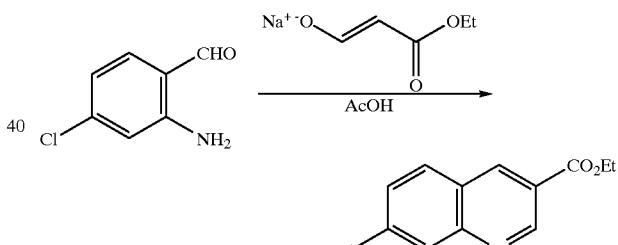

7-Chloro-quinoline-3-carboxylic acid ethyl ester

A solution of 4-chloro-2-aminobenzaldehyde (15 g, 96 mmol, 1 equiv) and 3-hydroxy-acrylic acid ethyl ester, sodium salt (6.65 g, 48 mmol, 0.5 equiv) in glacial acetic acid (175 mL), was heated at reflux for 3 hours. Additional 3-hydroxy-acrylic acid ethyl ester, sodium salt (6.65 grams, 48 mmol, 0.5 equivalents) was added and the reaction was heated at reflux for another 2.5 hours. Additional 3-hydroxy-acrylic acid ethyl ester, sodium salt (4 g, 28.8 mmol, 0.3 equiv) was added and the reaction was heated at reflux for an additional 12 hours. Additional 3-hydroxy-acrylic acid ethyl ester, sodium salt (4 g, 28.8 mmol, 0.3 equiv) was added and the reaction was heated at reflux for 4 hours. The reaction mixture was cooled and concentrated in vacuo. The residue was dissolved in ethyl acetate (200 mL) and washed with saturated sodium bicarbonate solution (200 mL). The organic layer was then washed with brine (200 mL), dried over sodium sulfate, and treated with activated charcoal (Darco G-60®) (20 g). The mixture was filtered through diatomaceous earth. Silica gel (15 g) (EM Science, Gibbstown, N.J., 230–400 mesh, 0.04–0.06 mm particle size) was added to the solution and stirred for 3 hours. The slurry was filtered, rinsed with toluene (100 ml) and then 10% ethyl acetate in toluene (200 mL). The combined organic layers were concentrated and the resulting solid was stirred in isopropanol overnight to yield 7-chloro-quinoline-3-carboxylic acid ethyl ester (3 g, 13% yield) as a pale yellow powder.

$^1$H NMR (CDCl$_3$) δ1.38 (m, 3H), 4.45 (m, 2H), 7.57 (dd, 1H, J=2.1, 8.7 Hz), 7.87 (d, 1H, J=8.7 Hz), 8.16 (d, 1H, J=1.3 Hz), 8.81 (d, 1H, J=2.1 Hz), 9.44 (d, 1H, J=2.1 Hz).

3-Hydroxy-acrylic acid ethyl ester, sodium salt can be made by the following procedure:

To a 20° C. slurry of sodium ethoxide (250 g, 3.49 mol, 1.5 equiv) and ethyl acetate (750 mL, 4.2 volumes) was dropwise added ethyl formate (178 g, 2.33 mol, 1 equiv) while keeping the internal temperature below 35° C. with external cooling. The resulting light tan slurry was stirred for 4 hours at room temperature and then diluted with hexanes (200 mL, 1.12 volumes). The off-white solids were collected by suction filtration and dried in vacuo at 20°–25° C. to provide 3-hydroxy-acrylic acid ethyl ester, sodium salt (204.4 g, 63.5%)

Step 3

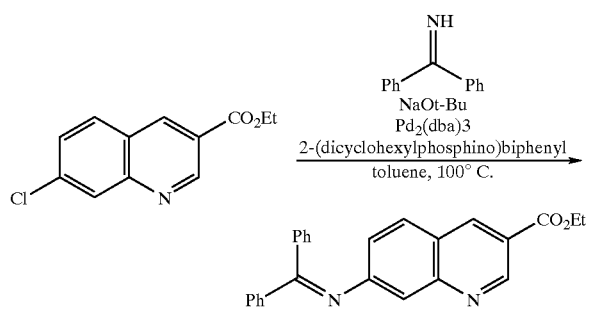

7-(Benzhydrylidene-amino)-quinoline-3-carboxylic acid ethyl ester

7-Chloro-quinoline-3-carboxylic acid ethyl ester (1 g, 4.24 mmol, 1 equiv), dry sodium t-butoxide (571 mg, 5.94 mmol, 1.4 equiv), tris(dibenzylideneacetone)dipalladium (19.5 mg, 21.2 μmol, 1 mol % equiv), and 2-(dicylcohexylphosphino)biphenyl (30 mg, 84.8 μmol, 4 mol % equiv) were placed in a round bottom flask with a magnetic stir bar. The flask was flushed with nitrogen. Benzophenone imine (783 μL, 4.66 mmol, 1.1 equiv) and toluene (8.5 mL) were added. The flask was fitted with a reflux condenser and the reaction was heated at 100° C. for 12 hours. The reaction mixture was cooled to room temperature and diluted with ethyl acetate (20 mL). The reaction mixture was washed with a saturated sodium bicarbonate solution (25 mL), saturated ammonium chloride solution (25 mL), and brine (25 mL). The organic layer was dried over sodium sulfate and then treated with activated charcoal (Darco G-60®) (1 g). The mixture was filtered through diatomaceous earth and concentrated. The residue was stirred in a minimal amount of isopropanol (about 2 mL) to provide 7-(benzhydrylidene-amino)-quinoline-3-carboxylic acid ethyl ester (199 mg, 12%) as a pale yellow solid.

MS(APCI)381 (M+1)$^{+1}$H NMR (CDCl$_3$) δ1.42 (t, 3H, J=7.1 Hz), 4.42 (q, 2H, J=7.1 Hz), 7.06 (dd, 1H, J=2.1, 8.7 Hz), 7.14–7.22 (m, 5H), 7.38–7.51 (m, 4H), 7.69 (d, 1H, J=8.7 Hz), 7.79 (d, 2H, J=7.1 Hz), 8.67 (d, 1H, J=2.1 Hz), 9.31 (d, 1H, J=2.1 Hz).

Step 4

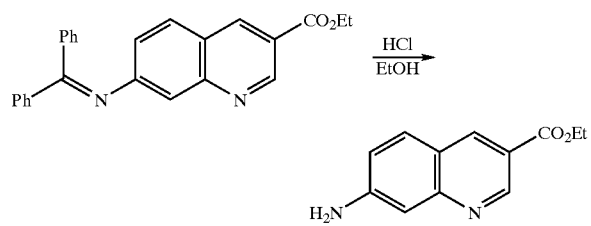

7-Amino-quinoline-3-carboxylic acid ethyl ester

Concentrated hydrochloric acid (1 mL, 2.5 volumes) was added to a solution of 7-(benzhydrylidene-amino)-quinoline-3-carboxylic acid ethyl ester (400 mg, 1.05 mmol, 1 equiv) in ethanol (4 mL, 10 volumes). The solution was stirred at room temperature for three hours and then concentrated. The residue was dissolved in ethyl acetate (20 mL, 50 volumes) and the organic layer was washed with 1 N hydrochloric acid (5×25 mL). The pH of the combined aqueous layer was then adjusted to about 8 with solid sodium hydroxide. The aqueous layer was then extracted with ethyl acetate (3×50 mL). The combined organic layers were dried over sodium sulfate and concentrated to provide 7-amino-quinoline-3-carboxylic acid ethyl ester (155 mg, 68%) as a yellow solid. The crude solid can be further purified by flash column chromatography using silica gel (EM Science, Gibbstown, N.J., 230–400 mesh) in 60% ethyl acetate in hexanes if desired.

MS(APCI)217 (M+1)$^{+1}$H NMR (DMSO-d$_6$) δ1.32 (t, 3H, J=7.0 Hz), 4.31 (q, 2H, J=7.1 Hz), 6.27 (br s, 2H), 6.92 (s, 1H), 7.02 (d, 1H, J=8.7 Hz), 7.77 (d, 1H, J=8.7 Hz), 8.56 (s, 1H), 8.99 (d, 1H, J=2.1 Hz).

Step 5

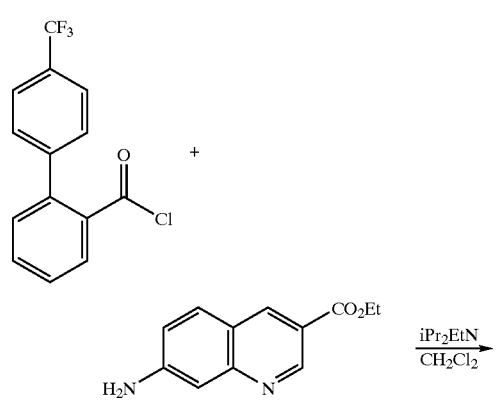

-continued

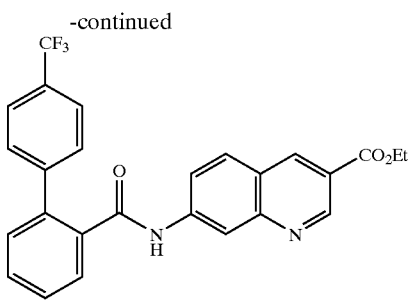

7-[(4'-Trifluoromethyl-biphenyl-2-carbonyl)-amino]-quinoline-3-carboxylic acid ethyl ester To a mixture of 7-amino-quinoline-3-carboxylic acid ethyl ester (11 g, 51 mmol, 1 equiv), dichloroethane (220 mL, 20 volumes), and diisopropylethylamine (13.15 g, 101.7 mmol, 2 equiv) was slowly added a solution of 4'-trifluoromethyl-biphenyl-2-carbonyl chloride (17.38 g, 61 mmol, 1.2 equiv) dissolved in dichloroethane (30 mL, 2.7 volumes). The reaction was heated at 84° C. overnight and then cooled to room temperature. The reaction mixture was washed with 1 N hydrochloric acid (2×150 mL) and the aqueous layer was back extracted with dichloroethane (1×150 mL). The combined organic layers were washed with 1 N sodium hydroxide (2×150 mL), water (150 mL), and saturated sodium chloride (2×150 mL). The combined organic layers were dried over sodium sulfate and concentrated in vacuo to give a red-brown oil. The oil was dissolved in hot toluene (32 mL) and isopropyl ether (16 mL) and the resulting solution was allowed to cool with stirring to give a beige slurry. The solids were collected by filtration to give 7-[(4'-trifluoromethyl-biphenyl-2-carbonyl)-amino]-quinoline-3-carboxylic acid ethyl ester (13.8 g, 58.4%).

Step 6

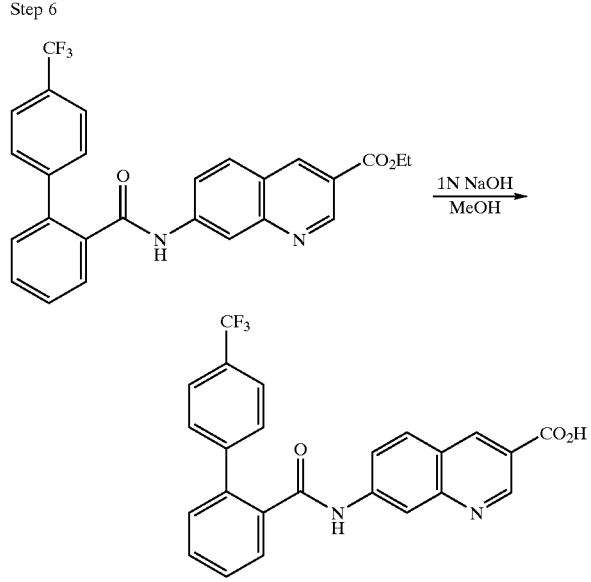

7-[(4'-trifluoromethyl-biphenyl-2-carbonyl)-amino]-quinoline-3-carboxylic acid

To a solution of 7-[(4'-trifluoromethyl-biphenyl-2-carbonyl)-amino]-quinoline-3-carboxylic acid ethyl ester (50 g, 114.5 mmol, 1 equiv) and methanol (750 mL, 15 volumes) was slowly added 1 N sodium hydroxide (220 mL, 4.4 volumes). After stirring at room temperature for 2 hours, the reaction was concentrated in vacuo. Water (750 mL) was added to the residue and the pH was adjusted to 5.0 using 1 N hydrochloric acid (250 mL). The resulting slurry was stirred for 30 minutes and the precipitated solids were collected by filtration and dried in vacuo and then dissolved in methanol (75 mL) and ethyl acetate (675 mL). The solution was dried over sodium sulfate and filtered, and concentrated in vacuo. The residue was slurried in ethyl acetate (250 mL). The solids were collected by filtration to give 7-[(4'-trifluoromethyl-biphenyl-2-carbonyl)-amino]-quinoline-3-carboxylic acid (28.1 g, 60%).

Step 7

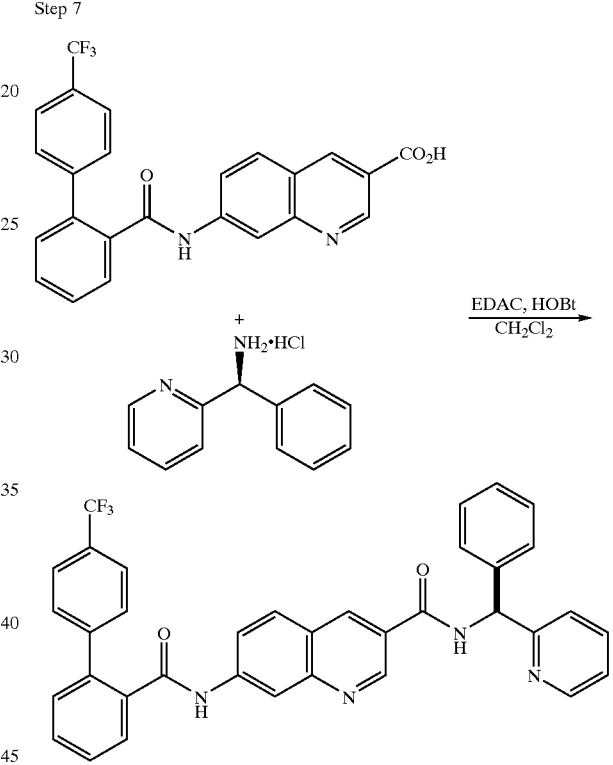

To a suspension of 7-[(4'-trifluoromethyl-biphenyl-2-carbonyl)-amino]-3-carboxylic acid (10 g, 22.9 mmol, 1 equiv) and methylene chloride (168 mL, 16.8 volumes) was added (S)-phenyl-(2-pyridyl)-methylamine, hydrochloric acid salt (6.5 g, 29.8 mmol, 1.3 equiv), 3-ethyl-1-(3-diethylaminopropyl)-carbodiimide hydrochloride (EDAC) (5.3 g, 27.5 mmol, 1.2 equiv), and hydroxy benzotriazole (HOBT) (3.3 g, 24.1 mmol, 1.05 equiv). Diisopropylethylamine (11.97 g, 92.6 mmol, 4.04 equiv) was added dropwise. The resulting solution was allowed to stir for 12 hours at room temperature. The solution was then extracted with 0.5 N hydrochloric acid (3×80 mL), saturated sodium hydrogen carbonate (2×80 mL) and saturated sodium chloride (80 mL). The organic layer was dried over sodium sulfate and concentrated in vacuo to give (+)-(S)-7-[(4'-trifluoromethyl-biphenyl-2-carbonyl)-amino]-quinoline-3-carboxylic acid (phenyl-pyridin-2-yl-methyl)-amide (12.2 g, 88.4%).

Method 3

Step 1

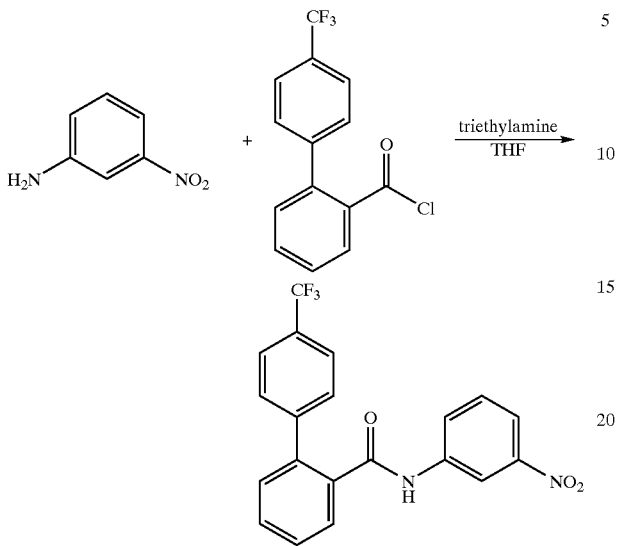

4'-Trifluoromethyl-biphenyl-2-carboxylic acid (3-nitro-phenyl)-amide

To a solution of 3-nitroaniline (28.8 g, 209 mmol, 1 equiv) in THF (1000 mL, 35 volumes), was added triethylamine (70 mL, 500 mmol, 2.4 equiv). 3-Nitroaniline can be obtained from Aldrich, Milwaukee, Wis. A solution of 4'-trifluoromethyl-biphenyl-2-carbonyl chloride (71.3 g, 250 mmol, 1.2 equiv) in THF (250 mL, 3.5 volumes) was added dropwise over 30 minutes. The reaction was stirred at room temperature for 48 hours. The slurry was then filtered through diatomaceous earth and the filtrate was concentrated. Water (700 mL, 24 volumes) was added and the slurry was stirred at room temperature for 12 hours. The solids were collected by filtration and dried under vacuum at 40° C. to provide 4'-trifluoromethyl-biphenyl-2-carboxylic acid (3-nitro-phenyl)-amide (80.7 g, 100%) as a pale yellow powder.

MS(APCI)387(M+1)$^+$; 385(M−1)$^{-1}$H NMR (DMSO-d$_6$) δ7.25–7.77 (m, 9H), 7.85 (dd, 1H, J=2.0, 8.3 Hz), 7.92 (dd, 1H, J=2.1,7.9 Hz), 8.56 (t, 1H, J=2.0 Hz), 10.92 (s, 1H).

Step 2

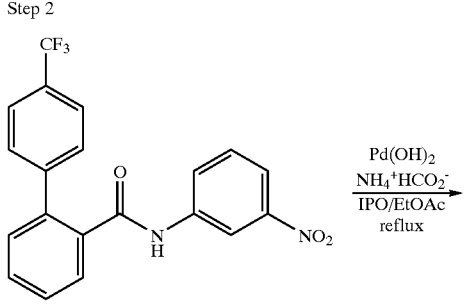

4'-Trifluoromethyl-biphenyl-2-carboxylic acid (3-amino-phenyl)-amide

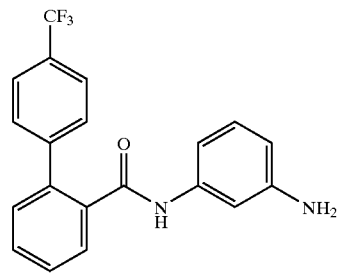

Ammonium formate (16.3 g, 258 mmol, 3 equiv), followed by Pearlman's catalyst [Pd(OH)$_2$] (6.03 g, 4.30 mmol, 0.05 equiv) was added to a solution of 4'-trifluoromethyl-biphenyl-2-carboxylic acid (3-nitro-phenyl)-amide (33.2 g, 85.9 mmol, 1 equiv) in isopropanol (330 mL, 10 volumes) and ethyl acetate (170 mL, 5 volumes). The mixture was heated at reflux for 3 hours. After cooling, THF (500 mL) was added to the reaction mixture to help solublize the product. The reaction mixture was filtered through diatomaceous earth and the filtrate was concentrated to about 100 mL. Ethyl acetate (600 mL) and THF (200 mL) were added. The organic layer was washed with saturated sodium bicarbonate solution (300 mL), dried over sodium sulfate, filtered, and concentrated to afford 4'-trifluoromethyl-biphenyl-2-carboxylic acid (3-amino-phenyl)-amide (28.7 g, 94%) as an off-white solid.

MS(APCI)357 (M+1)$^+$; 355(M−1)$^{-1}$H NMR (DMSO-d$_6$) δ5.00 (br s, 2H), 6.22 (dd, 1H, J=1.7, 9.5 Hz), 6.55 (d, 1H, J=8.7 Hz), 6.84 (t, 1H, J=7.9 Hz), 6.90 (s, 1H), 7.04–7.61 (m, 6H), 7.73 (d, 2H, J=8.3 Hz), 10.05(s, 1H).

Step 3

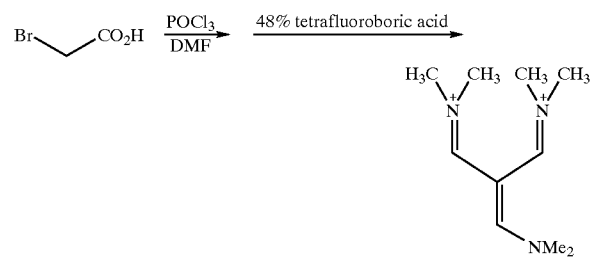

2-Dimethylaminomethylene-1,3-bis(dimethylimmonio)propane bis(tetrafluoroborate)

To a 2 L 3-neck round bottom flask equipped with a reflux condenser and a mechanical stirrer, was added bromoacetic acid (50 g, 360 mmol, 1 equiv) and phosphorus oxychloride (100 mL, 1.08 mol, 3 equiv). The solution was cooled to 0° C. and DMF (167 mL, 2.16 mol, 6 equiv) was added dropwise over 30 minutes via an addition funnel. The resulting solution was heated at 110° C. for 3 hours, then was cooled to 0° C. A solution of aqueous 48% tetrafluoroboric acid in MeOH (200 mL) was added slowly over 1 hour via an addition funnel. Isopropanol (200 mL) was added to the dark viscous solution. Solids precipitated out and the slurry was stirred at 0° C. for 2 hours. The solids were collected by filtration to provide 2-dimethylaminomethylene-1,3-bis (dimethylimmonio)propane bis(tetrafluoroborate) (94.2 g, 73%) as a pale yellow solid.

$^1$H NMR (DMSO-d$_6$) δ3.35 (s, 6H), 3.51 (s, 12H), 8.38 (s, 3H).

Step 4

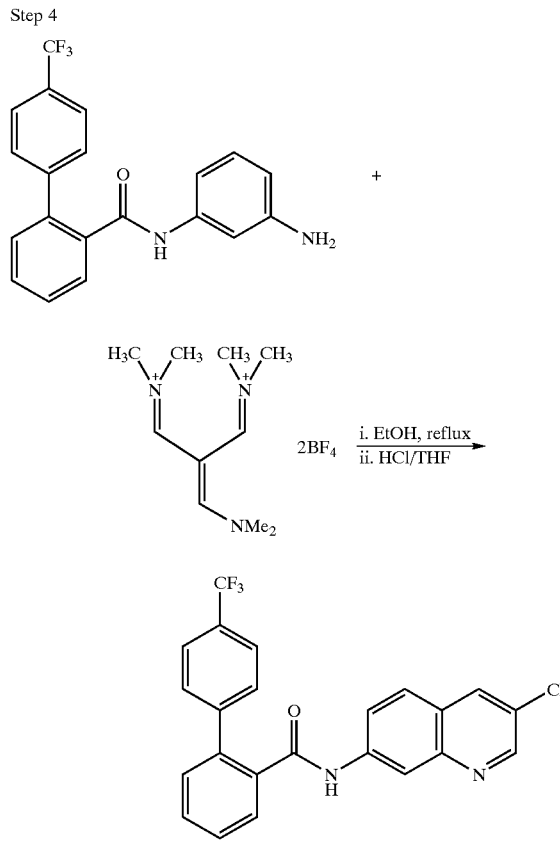

4'-Trifluoromethyl-biphenyl-2-carboxylic acid (3-formyl-quinolin-7-yl)-amide

A slurry of 4'-trifluoromethyl-biphenyl-2-carboxylic acid (3-amino-phenyl)-amide (6.5 g, 18.2 mmol, 1 equiv) and 2-dimethylaminomethylene-1,3-bis(dimethylimmonio) propane bis(tetrafluoroborate) (19.5 g, 54.7 mmol, 3 equiv) in ethanol (200 mL, 30 volumes) was heated at reflux for 24 hours. The reaction became homogeneous after heating for 4 hours. The solution was concentrated and the residue was dissolved in THF (100 mL, 15 volumes) and 1 N HCl (100 mL, 15 volumes). The reaction mixture was stirred at room temperature for 3 hours, then poured into a saturated solution of sodium bicarbonate (100 mL), and extracted with ethyl acetate (2×100 mL). The combined organic layers were dried over sodium sulfate, treated with activated charcoal, filtered, (6.5 g, 1 weight equiv) and concentrated to afford 4'-trifluoromethyl-biphenyl-2-carboxylic acid (3-formyl-quinolin-7-yl)-amide (7.65 g, 100% crude yield)

as a yellow foam. The crude product was clean by $^1$H NMR and used in the next step without further purification.

MS(APCI)421 (M+1)$^+$; 419(M−1)$^{−1}$ $^1$H NMR (DMSO-d$_6$) δ7.54–7.77 (m, 9H), 8.10 (d, 1H, J=8.7 Hz), 8.46 (s, 1H), 8.80 (d, 1H, J=2.1 Hz), 9.20 (d, 1H, J=2.1 Hz), 10.20 (s, 1H), 10.95 (s, 1H).

Step 5

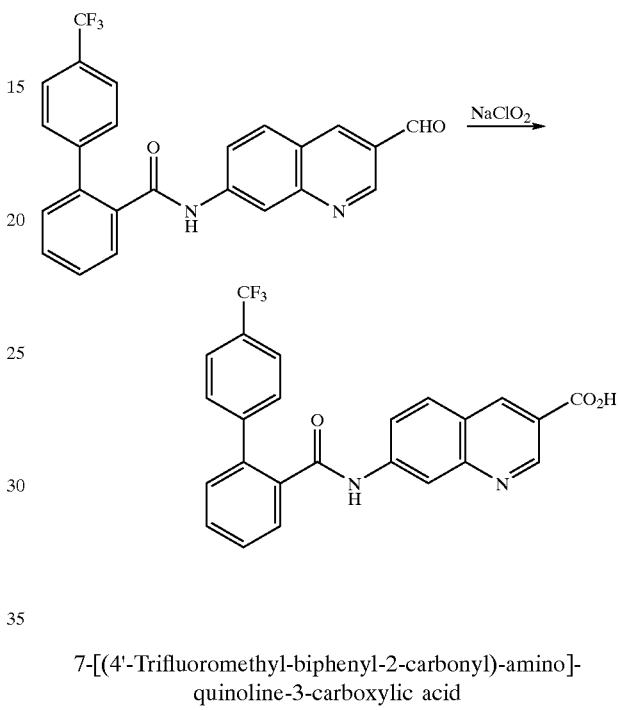

7-[(4'-Trifluoromethyl-biphenyl-2-carbonyl)-amino]-quinoline-3-carboxylic acid

To a solution of 4'-trifluoromethyl-biphenyl-2-carboxylic acid (3-formyl-quinolin-7-yl)-amide (7.65 g, 18.2 mmol, 1 equiv) in acetonitrile (100 mL, 15 volumes) was added an aqueous solution of potassium dihydrogen phosphate (1.25 M, 72.8 mL, 91 mmol, 5 equiv), followed by sodium chlorite (6.17 g, 54.6 mmol, 3 equiv). The slurry was stirred at room temperature for 12 hours. An aqueous solution of sodium sulfite (1 M, 75 mL, 75 mmol, 4.1 equiv) was added and the resulting slurry was stirred at room temperature for 15 minutes. 1 N HCl (50 mL) was added to bring the pH to about 3 to 4. The aqueous layer was extracted with ethyl acetate (2×100 mL). The combined organic layers were dried over sodium sulfate and concentrated to about 75 mL of ethyl acetate. Hexanes (about 75 mL) was added to the slurry and the resulting slurry was allowed to stir at room temperature for 2 hours. The precipitate was collected by filtration to provide 7-[(4'-trifluoromethyl-biphenyl-2-carbonyl)-amino]-quinoline-3-carboxylic acid (6.32 g, 80% over two steps) as a yellow powder.

MS(APCI)437 (M+1)$^+$; 435(M−1)$^{−1}$ $^1$H NMR (DMSO-d$_6$) δ7.54–7.74 (m, 9H), 8.08 (d, 1H, J=8.7 Hz), 8.44 (s, 1H), 8.84 (d, 1H, J=1.7 Hz), 9.22 (d, 1H, J=2.0 Hz), 10.90 (s, 1H).

Step 6

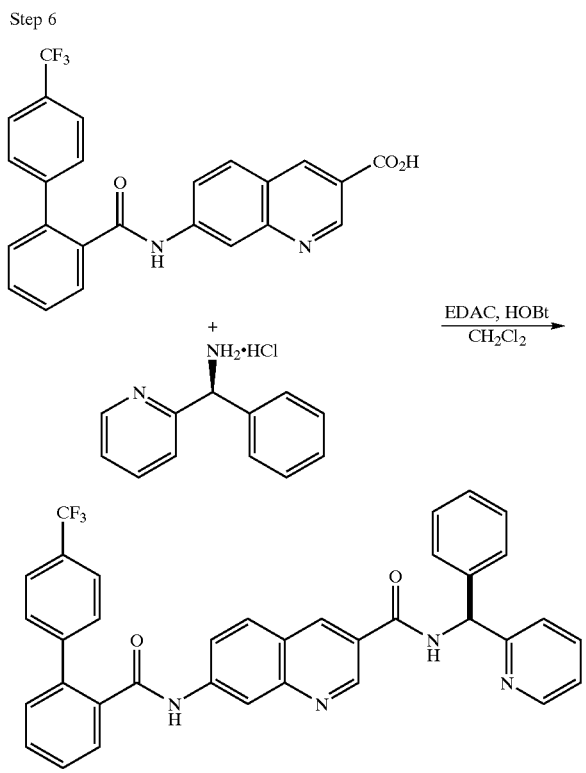

(+)-(S)-7-[(4'-Trifluoromethyl-biphenyl-2-carbonyl)-amino]-quinoline-3-carboxylic acid (phenyl-pyridin-2-yl-methyl)-amide To a suspension of 7-[(4'-trifluoromethyl-biphenyl-2-carbonyl)-amino]-3-carboxylic acid (10 g, 22.9 mmol, 1 equiv) and methylene chloride (168 mL, 16.8 volumes) was added (S)-phenyl-(2-pyridyl)-methylamine, hydrochloric acid salt (6.5 g, 29.8 mmol, 1.3 equiv), 3-ethyl-1-(3-diethylaminopropyl)-carbodiimide hydrochloride (EDAC) (5.3 g, 27.5 mmol, 1.2 equiv), and hydroxy benzotriazole (HOBT) (3.3 g, 24.1 mmol, 1.05 equiv). Diisopropylethylamine (11.97 g, 92.6 mmol, 4.04 equiv) was added dropwise. The resulting solution was allowed to stir for 12 hours at room temperature. The solution was then extracted with 0.5 N hydrochloric acid (3×80 mL), saturated sodium hydrogen carbonate (2×80 mL) and saturated sodium chloride (80 mL). The organic layer was dried over sodium sulfate and concentrated in vacuo to give (+)-(S)-7-[(4'-trifluoromethyl-biphenyl-2-carbonyl)-amino]-quinoline-3-carboxylic acid (phenyl-pyridin-2-yl-methyl)-amide (12.2 g, 88.4%).

Resolution of phenyl-(2-pyridyl)-methylamine

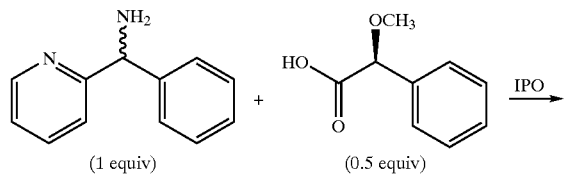

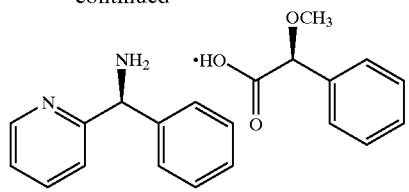

(S)-Phenyl-(2-pyridyl)-methylamine, (S)-(+)-α-methoxyphenylacetic acid salt (S)-(+)-α-Methoxyphenylacetic acid (22.5 g, 136 mmol, 0.5 equiv) was added to a solution of phenyl-(2-pyridyl)-methylamine (50 g, 271 mmol, 1 equiv) in isopropanol (800 mL, 16 volumes) and a precipitate formed. Racemic phenyl-(2-pyridyl)-methylamine can be obtained from Alfa Aesar, Ward Hill, Mass. After stirring overnight, the precipitate was collected to provide (S)-phenyl-(2-pyridyl)-methylamine, (S)-(+)-α-methoxyphenylacetic acid salt as a 75/25 ratio of enantiomeric salts. Recrystallization of the collected solid in 16 volumes of isopropanol improved the ratio to 95.3/4.7. An additional recrystallization in 10 volumes of ispropanol then improved the ratio to 99.6/0.4. (S)-Phenyl-(2-pyridyl)-methylamine, (S)-(+)-α-methoxyphenylacetic acid salt was isolated as a white solid (16.2 g, 34.2%).

Hydrochloride salt

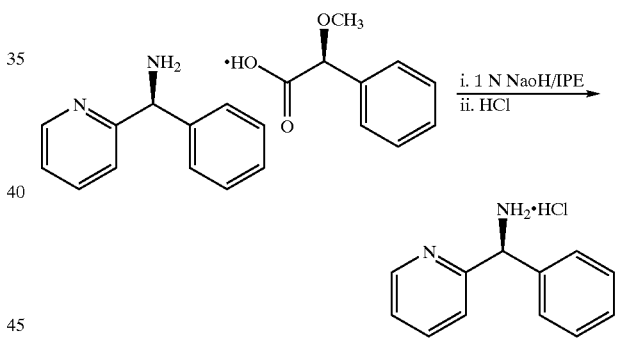

(S)-Phenyl-(2-pyridyl)-methylamine, hydrochloride salt

To a mixture of (S)-phenyl-(2-pyridyl)-methylamine, (S)-α-methoxyphenylacetic acid salt (10 g, 28.5 mmol, 1 equiv) and isopropyl ether (100 mL, 10 volumes) was added 1 N sodium hydroxide (1.14 g, 28.5 mmol, 1 equiv). The mixture was stirred until two transparent layers appeared (1 hour). The layers were separated and the aqueous layer was extracted with isopropyl ether (2×25 mL). The combined organic phases were concentrated in vacuo at 35° to 40° C. to 100 mL. Gaseous HCl (1.6 g, 44.4 mmol, 3 equiv) was bubbled into the solution and white solids precipitated immediately. After stirring the mixture for 15 hours with slow agitation, the solids were collected by filtration and dried in vacuo for 2 hours and 50° C. to give (S)-phenyl-(2-pyridyl)-methylamine, hydrochloric acid salt (5.0 g, 95.5%).

What is claimed is:

1. A method of resolving phenyl-(2-pyridyl)-methylamine to obtain (S)-phenyl-(2-pyridyl)-methylamine, (S)-(+)-α-methoxyphenylacetic acid salt, the method comprising the steps of:
   a. reacting phenyl-(2-pyridyl)-methylamine
      with (S)-(+)-α-methoxyphenylacetic acid in isopropanol, which results in a precipitate being formed; and
   b. isolating the precipitate, which is (S)-phenyl-(2-pyridyl)-methylamine, (S)-(+)-α-methoxyphenylacetic acid salt.

2. The method of claim 1 wherein of the (S)-(+)-α-methoxyphenylacetic acid is present in the reaction in an amount in the range of about 0.5 equivalents with respect to the amine.

3. The method of claim 1 wherein the isolated precipitate is purified by recrystallization.

4. The method of claim 1 wherein the (S)-phenyl-(2-pyridyl)-methylamine, (S)-(+)-α-methoxyphenylacetic acid salt is converted to the (S)-phenyl-(2-pyridyl)-methylamine hydrochloride salt.

* * * * *